US012569125B2

(12) United States Patent
Takahashi et al.

(10) Patent No.: US 12,569,125 B2
(45) Date of Patent: Mar. 10, 2026

(54) MEDICAL IMAGING SYSTEM, MEDICAL IMAGING PROCESSING METHOD, AND MEDICAL INFORMATION PROCESSING APPARATUS

(71) Applicant: Sony Group Corporation, Tokyo (JP)

(72) Inventors: Yasuaki Takahashi, Tokyo (JP); Keisuke Uyama, Tokyo (JP)

(73) Assignee: Sony Group Corporation, Tokyo (JP)

( * ) Notice: Subject to any disclaimer, the term of this patent is extended or adjusted under 35 U.S.C. 154(b) by 499 days.

(21) Appl. No.: 17/608,525

(22) PCT Filed: Jun. 19, 2020

(86) PCT No.: PCT/JP2020/024060
§ 371 (c)(1),
(2) Date: Nov. 3, 2021

(87) PCT Pub. No.: WO2020/256089
PCT Pub. Date: Dec. 24, 2020

(65) Prior Publication Data
US 2022/0225860 A1     Jul. 21, 2022

(30) Foreign Application Priority Data

Jun. 21, 2019     (JP) ................................. 2019-115405

(51) Int. Cl.
*A61B 1/06*         (2006.01)
*A61B 1/00*         (2006.01)
(Continued)

(52) U.S. Cl.
CPC ........ *A61B 1/0638* (2013.01); *A61B 1/00006* (2013.01); *A61B 1/000094* (2022.02);
(Continued)

(58) Field of Classification Search
CPC .......... A61B 1/00006; A61B 1/000094; A61B 1/000096; A61B 1/0005; A61B 1/043;
(Continued)

(56) References Cited

U.S. PATENT DOCUMENTS

2005/0182321 A1     8/2005   Frangioni
2005/0283065 A1     12/2005   Babayoff
(Continued)

FOREIGN PATENT DOCUMENTS

CN         101729784 A     6/2010
CN         103356155 A     10/2013
(Continued)

OTHER PUBLICATIONS

International Search Report and Written Opinion mailed on Sep. 24, 2020, received for PCT Application PCT/JP2020/024060, Filed on Jun. 19, 2020, 11 pages.

*Primary Examiner* — Michael J Carey
*Assistant Examiner* — Maria Christina Talty
(74) *Attorney, Agent, or Firm* — XSENSUS LLP

(57) ABSTRACT

A medical imaging system includes a light source configured to irradiate a surgical field with observation light of a first wavelength band or special light of a second wavelength band different from the first wavelength band; an image capture device configured to generate a special light image based on reflected special light that is the special light reflected from at least a portion of the surgical field and received by the image capture device; and a control processing circuit configured to generate three-dimensional information including three-dimensional coordinate information about the surgical field based on the special light image.

20 Claims, 18 Drawing Sheets

(51) Int. Cl.

| | | |
|---|---|---|
| *A61B 1/04* | (2006.01) |
| *A61B 1/313* | (2006.01) |
| *G06T 7/00* | (2017.01) |
| *G06T 7/33* | (2017.01) |
| *G06T 7/73* | (2017.01) |

(52) U.S. Cl.

CPC ...... *A61B 1/000096* (2022.02); *A61B 1/0005* (2013.01); *A61B 1/043* (2013.01); *G06T 7/0012* (2013.01); *G06T 7/33* (2017.01); *G06T 7/73* (2017.01); *A61B 1/3132* (2013.01); *G06T 2207/10048* (2013.01); *G06T 2207/10068* (2013.01); *G06T 2207/30101* (2013.01)

(58) Field of Classification Search

CPC ............... A61B 1/0638; A61B 1/3132; G06T 2207/10048; G06T 2207/10068; G06T 2207/30101; G06T 7/0012; G06T 7/33; G06T 7/73

See application file for complete search history.

(56) References Cited

U.S. PATENT DOCUMENTS

| | | | |
|---|---|---|---|
| 2010/0039534 A1 | 2/2010 | Hart et al. |
| 2014/0336461 A1 | 11/2014 | Reiter et al. |
| 2015/0221089 A1 | 8/2015 | Funabasama |
| 2015/0223725 A1* | 8/2015 | Engel ..................... A61B 34/20 600/417 |
| 2016/0007009 A1* | 1/2016 | Offenberg ........... H04N 13/254 348/46 |
| 2016/0203602 A1 | 7/2016 | Hayashi |
| 2017/0172662 A1 | 6/2017 | Panescu et al. |
| 2017/0209031 A1 | 7/2017 | Nakamura |
| 2018/0342074 A1* | 11/2018 | Sakamoto ................. G06T 5/70 |
| 2019/0043215 A1* | 2/2019 | Ito .......................... A61B 34/20 |
| 2019/0053691 A1* | 2/2019 | Hansen ................. A61B 17/29 |
| 2020/0197100 A1 | 6/2020 | Leung |

FOREIGN PATENT DOCUMENTS

| | | | |
|---|---|---|---|
| CN | 104364606 A | 2/2015 |
| CN | 105279731 A | 1/2016 |
| CN | 107847130 A | 3/2018 |
| CN | 107925739 A | 4/2018 |
| CN | 109561251 A | 4/2019 |
| EP | 1607064 A2 | 12/2005 |
| EP | 2857793 A1 | 4/2015 |
| JP | 2009261798 A | 11/2009 |
| JP | 2012165838 A | 9/2012 |
| JP | 2016093210 A | 5/2016 |
| JP | 2020010763 A | 1/2020 |
| WO | WO-2016181454 A1 | 11/2016 |
| WO | WO-2016194178 A1 | 12/2016 |
| WO | 2017/168986 A1 | 10/2017 |
| WO | WO-2018008136 A1 | 1/2018 |

* cited by examiner

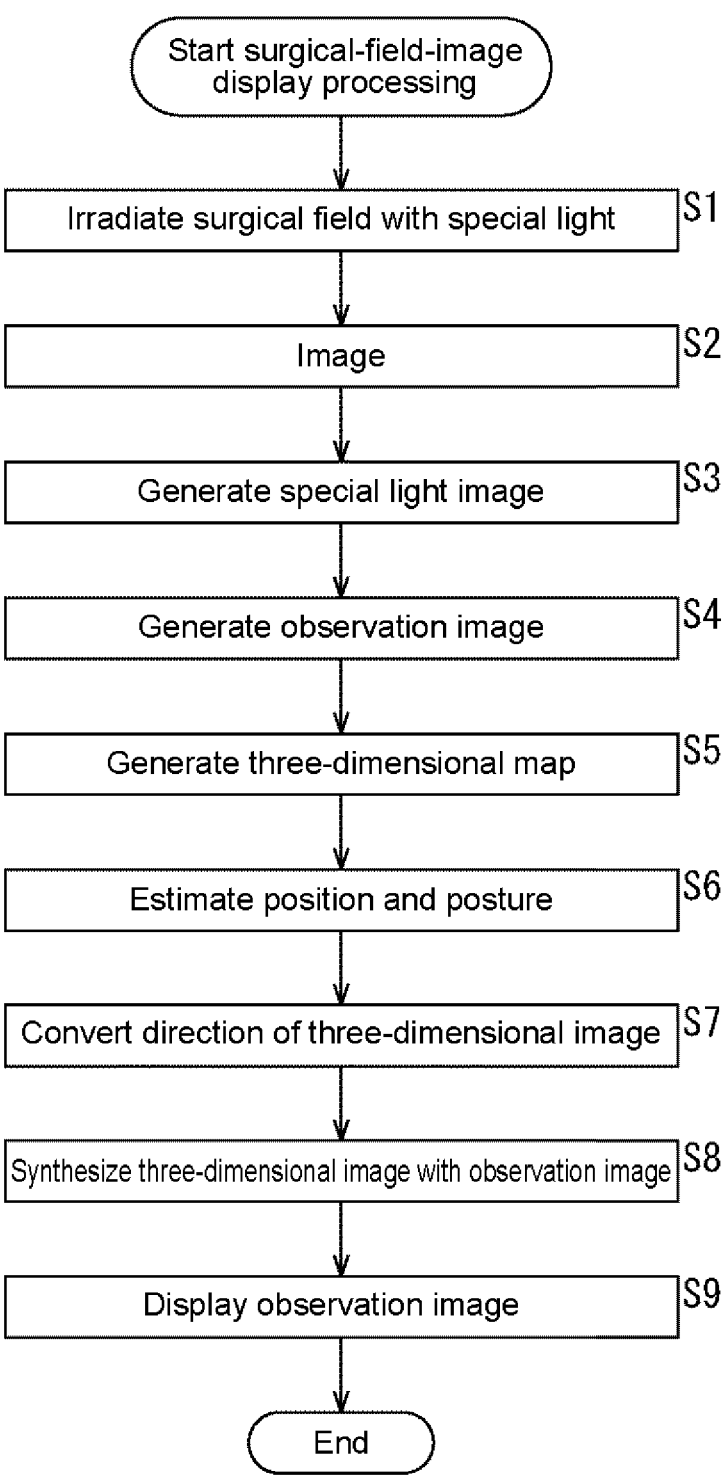

Start surgical-field-image display processing

Irradiate surgical field with special light  S1

Image  S2

Generate special light image  S3

Generate observation image  S4

Generate three-dimensional map  S5

Estimate position and posture  S6

Convert direction of three-dimensional image  S7

Synthesize three-dimensional image with observation image  S8

Display observation image  S9

End

FIG.4

Feature point $X_t^n$

Feature point $Y_t^m$

Leave only feature points with high reliability

Feature point $Z_t^1$

Feature point $Z_t^p$

FIG.15

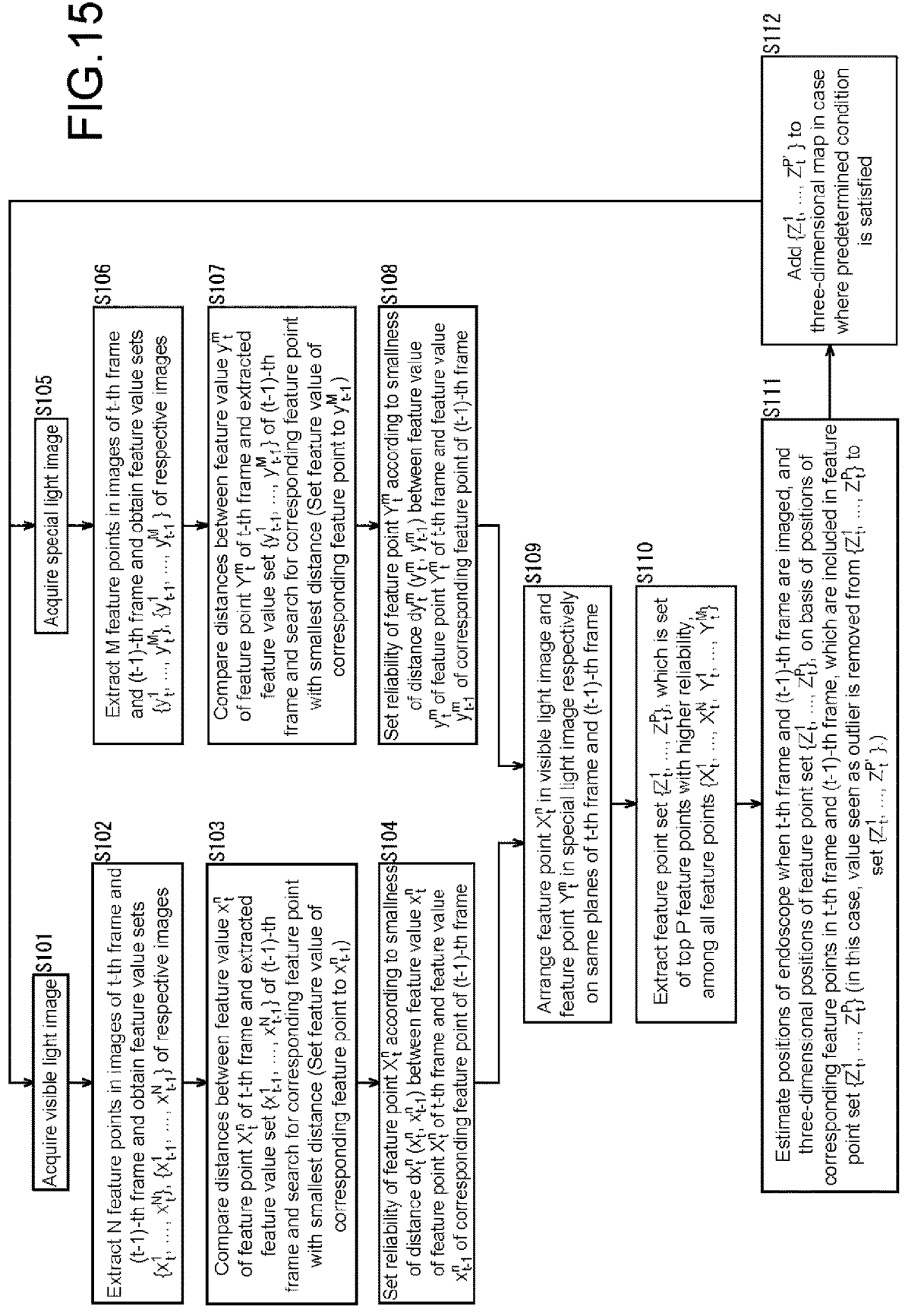

S101 Acquire visible light image

S102 Extract N feature points in images of t-th frame and (t-1)-th frame and obtain feature value sets $\{x^1_t, ..., x^N_t\}, \{x^1_{t-1}, ..., x^N_{t-1}\}$ of respective images

S103 Compare distances between feature value $x^n_t$ of feature point $X^n_t$ of t-th frame and extracted feature value set $\{x^1_{t-1}, ..., x^N_{t-1}\}$ of (t-1)-th frame and search for corresponding feature point with smallest distance (Set feature value of corresponding feature point to $x^n_{t-1}$)

S104 Set reliability of feature point $X^n_t$ according to smallness of distance $dx^n_t$ ($x^n_t, x^n_{t-1}$) between feature value $x^n_t$ of feature point $X^n_t$ of t-th frame and feature value $x^n_{t-1}$ of corresponding feature point of (t-1)-th frame

S105 Acquire special light image

S106 Extract M feature points in images of t-th frame and (t-1)-th frame and obtain feature value sets $\{y^1_t, ..., y^M_t\}, \{y^1_{t-1}, ..., y^M_{t-1}\}$ of respective images

S107 Compare distances between feature value $y^m_t$ of feature point $Y^m_t$ of t-th frame and extracted feature value set $\{y^1_{t-1}, ..., y^M_{t-1}\}$ of (t-1)-th frame and search for corresponding feature point with smallest distance (Set feature value of corresponding feature point to $y^M_{t-1}$)

S108 Set reliability of feature point $Y^m_t$ according to smallness of distance $dy^m_t$ ($y^m_t, y^m_{t-1}$) between feature value $y^m_t$ of feature point $Y^m_t$ of t-th frame and feature value $y^m_{t-1}$ of corresponding feature point of (t-1)-th frame

S109 Arrange feature point $X^n_t$ in visible light image and feature point $Y^m_t$ in special light image respectively on same planes of t-th frame and (t-1)-th frame

S110 Extract feature point set $\{Z^1_t, ..., Z^P_t\}$, which is set of top P feature points with higher reliability, among all feature points $\{X^1_t, ..., X^N_t, Y^1_t, ..., Y^M_t\}$

S111 Estimate positions of endoscope when t-th frame and (t-1)-th frame are imaged, and three-dimensional positions of feature point set $\{Z^1_t, ..., Z^P_t\}$, on basis of positions of corresponding feature points in t-th frame and (t-1)-th frame, which are included in feature point set $\{Z^1_t, ..., Z^P_t\}$ (in this case, value seen as outlier is removed from $\{Z^1_t, ..., Z^P_t\}$ to set $\{Z^1_t, ..., Z^{P'}_t\}$)

S112 Add $\{Z^1_t, ..., Z^{P'}_t\}$ to three-dimensional map in case where predetermined condition is satisfied

FIG.16

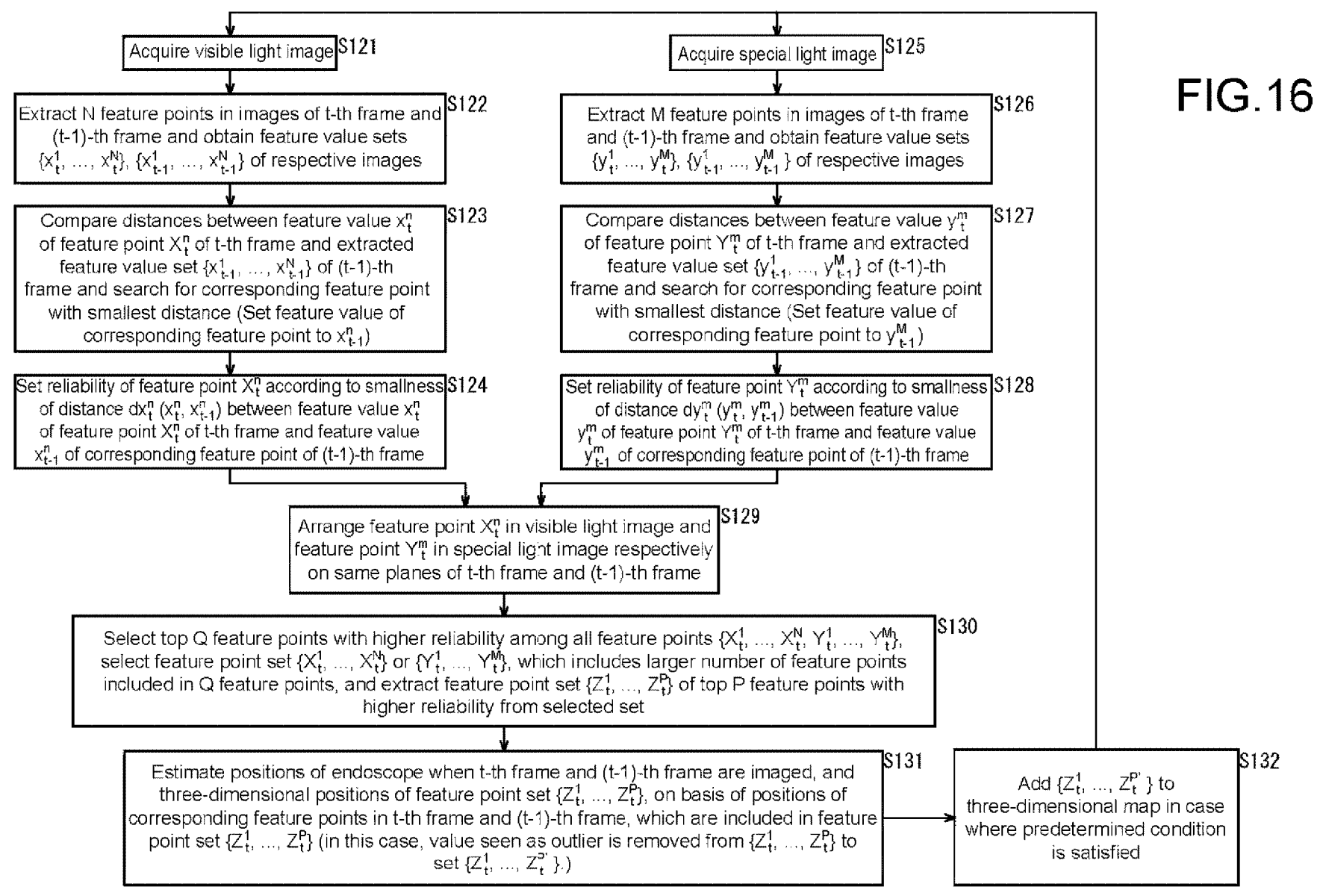

Acquire visible light image $S121$

Acquire special light image $S125$

Extract N feature points in images of t-th frame and (t-1)-th frame and obtain feature value sets $\{x_t^1, ..., x_t^N\}, \{x_{t-1}^1, ..., x_{t-1}^N\}$ of respective images $S122$ Extract M feature points in images of t-th frame and (t-1)-th frame and obtain feature value sets $\{y_t^1, ..., y_t^M\}, \{y_{t-1}^1, ..., y_{t-1}^M\}$ of respective images $S126$ Compare distances between feature value $x_t^n$ of feature point $X_t^n$ of t-th frame and extracted feature value set $\{x_{t-1}^1, ..., x_{t-1}^N\}$ of (t-1)-th frame and search for corresponding feature point with smallest distance (Set feature value of corresponding feature point to $x_{t-1}^n$) $S123$ Compare distances between feature value $y_t^m$ of feature point $Y_t^m$ of t-th frame and extracted feature value set $\{y_{t-1}^1, ..., y_{t-1}^M\}$ of (t-1)-th frame and search for corresponding feature point with smallest distance (Set feature value of corresponding feature point to $y_{t-1}^M$) $S127$ Set reliability of feature point $X_t^n$ according to smallness $S124$ of distance $dx_t^n$ $(x_t^n, x_{t-1}^n)$ between feature value $x_t^n$ of feature point $X_t^n$ of t-th frame and feature value $x_{t-1}^n$ of corresponding feature point of (t-1)-th frame Set reliability of feature point $Y_t^m$ according to smallness $S128$ of distance $dy_t^m$ $(y_t^m, y_{t-1}^m)$ between feature value $y_t^m$ of feature point $Y_t^m$ of t-th frame and feature value $y_{t-1}^m$ of corresponding feature point of (t-1)-th frame Arrange feature point $X_t^n$ in visible light image and feature point $Y_t^m$ in special light image respectively on same planes of t-th frame and (t-1)-th frame $S129$ Select top Q feature points with higher reliability among all feature points $\{X_t^1, ..., X_t^N; Y_t^1, ..., Y_t^M;\}$, select feature point set $\{X_t^1, ..., X_t^N\}$ or $\{Y_t^1, ..., Y_t^M;\}$, which includes larger number of feature points included in Q feature points, and extract feature point set $\{Z_t^1, ..., Z_t^P\}$ of top P feature points with higher reliability from selected set $S130$ Estimate positions of endoscope when t-th frame and (t-1)-th frame are imaged, and three-dimensional positions of feature point set $\{Z_t^1, ..., Z_t^P\}$, on basis of positions of corresponding feature points in t-th frame and (t-1)-th frame, which are included in feature point set $\{Z_t^1, ..., Z_t^P\}$ (in this case, value seen as outlier is removed from $\{Z_t^1, ..., Z_t^P\}$ to set $\{Z_t^1, ..., Z_t^{P'}\}$) $S131$ Add $\{Z_t^1, ..., Z_t^{P'}\}$ to three-dimensional map in case where predetermined condition is satisfied $S132$

MEDICAL IMAGING SYSTEM, MEDICAL IMAGING PROCESSING METHOD, AND MEDICAL INFORMATION PROCESSING APPARATUS

CROSS-REFERENCE TO RELATED APPLICATIONS

The present application is based on PCT filing PCT/JP2020/024060, filed Jun. 19, 2020, which claims priority to JP 2019-115405, filed Jun. 21, 2019, the entire contents of each are incorporated herein by reference.

TECHNICAL FIELD

The present technology relates to a medical observation system, a medical observation method, and an information processing apparatus, and particularly to a medical observation system, a medical observation method, and an information processing apparatus that are capable of obtaining three-dimensional information with high reliability.

BACKGROUND ART

In a surgery using medical observation apparatuses such as endoscopes and microscopes, the following technique is proposed: three-dimensional information of a surgical field is generated on the basis of image information or sensor information, and useful information for the surgery is further provided to an operator by using the generated three-dimensional information.

For example, Patent Literature 1 discloses the technique of acquiring optical axis angle information of an endoscope by simultaneous localization and mapping (SLAM) and controlling the image quality of a display image.

CITATION LIST

Patent Literature

PTL 1: WO 2017/168986

SUMMARY OF INVENTION

Technical Problem

By the way, in the surgery using the endoscopes and the microscopes, there is a technique of discerning a blood vessel or a lesioned part at a deep part, which is difficult to see in a visible light image, on the basis of a special light image obtained using special light such as infrared (IR) light of a wavelength band different from the wavelength band of the visible light (white light).

The present technology has been made in view of the circumstances as described above and can provide three-dimensional information with high reliability.

Solution to Problem

According to an embodiment of the present technology, there is provided a medical imaging system includes a light source configured to irradiate a surgical field with observation light of a first wavelength band or special light of a second wavelength band different from the first wavelength band; an image capture device configured to generate a special light image based on reflected special light that is the special light reflected from at least a portion of the surgical field and received by the image capture device; and a control processing circuit configured to generate three-dimensional information including three-dimensional coordinate information about the surgical field based on the special light image.

According to another embodiment of the present technology, there is provided an information processing apparatus including a controller that generates three-dimensional information on the basis of a special light image, the special light image being obtained by capturing an image of a surgical field during irradiation with special light from a light source unit that irradiates the surgical field with observation light of a predetermined wavelength band or the special light of a wavelength band different from the predetermined wavelength band.

In the embodiment of the present technology, the surgical field is irradiated with observation light of a predetermined wavelength band or special light of a wavelength band different from the predetermined wavelength band, and three-dimensional information is generated on the basis of a special light image captured during irradiation with the special light.

In the other embodiment of the present technology, three-dimensional information is generated on the basis of a special light image, the special light image being obtained by capturing an image of a surgical field during irradiation with special light from a light source unit that irradiates the surgical field with observation light of a predetermined wavelength band or the special light of a wavelength band different from the predetermined wavelength band.

BRIEF DESCRIPTION OF DRAWINGS

FIG. 4 is a flowchart for describing surgical-field-image display processing.

FIG. 15 is a flowchart for describing the three-dimensional map generation/position and posture estimation processing performed in Step S56 of FIG. 11.

FIG. 16 is a flowchart for describing different three-dimensional map generation/position and posture estimation processing.

DESCRIPTION OF EMBODIMENTS

Hereinafter, embodiments for carrying out the present technology will be descried. The description will be given in the following order.

1. Medical Observation System
2. Special Light Simultaneous Localization and Mapping (SLAM)
3. Combination SLAM
4. Modified Example
5. Application Example <<Medical Observation System>>

<System Configuration>

Figure 1:
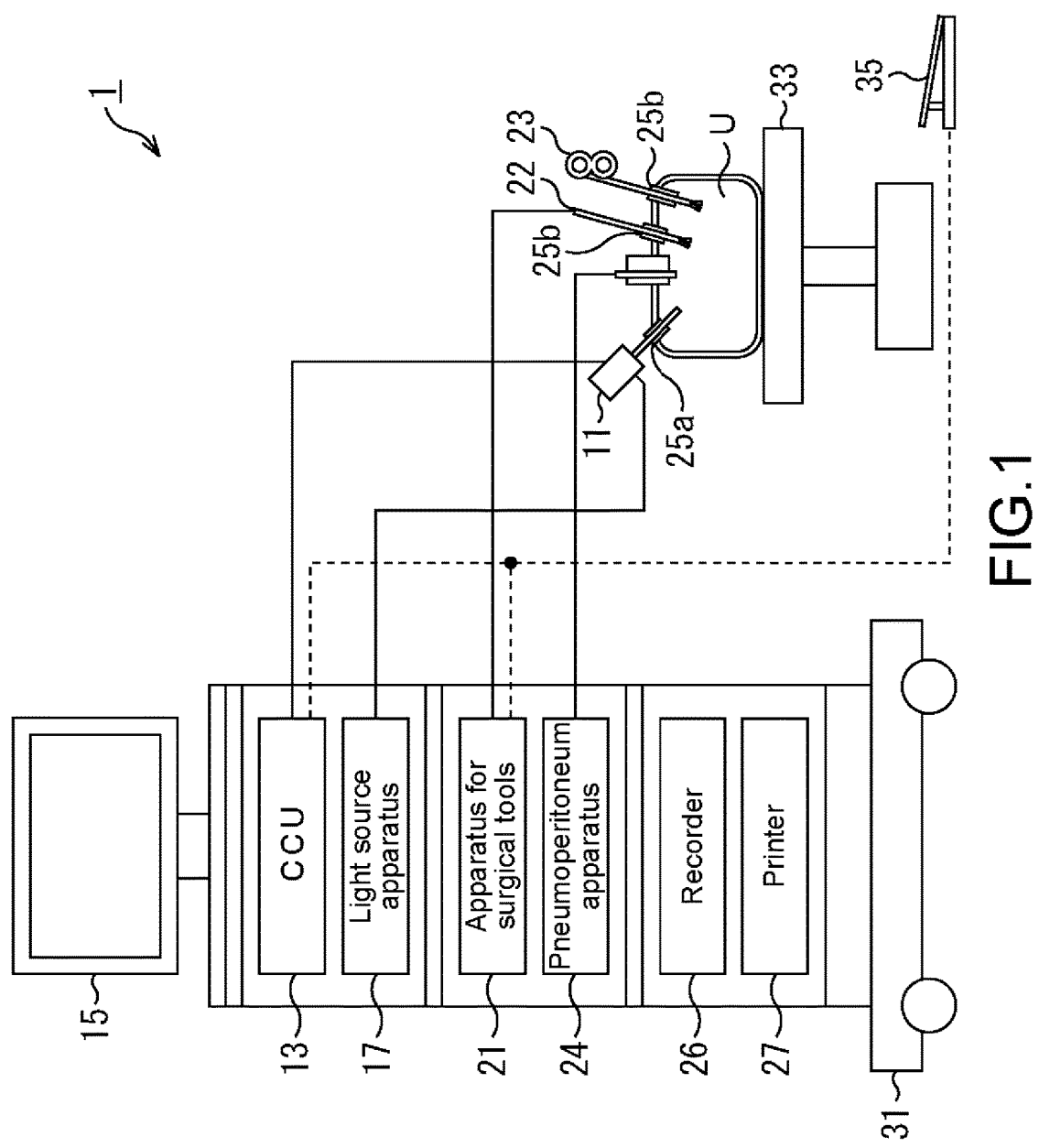
FIG. 1 is a diagram showing a configuration example of a medical observation system according to an embodiment of the present technology.

FIG. 1 is a diagram showing a configuration example of a medical observation system according to an embodiment of the present technology.

FIG. 1 shows an example of an endoscope surgery system used in an endoscopic surgery for an abdomen, which is performed instead of the existing laparotomy in a medical setting, for example.

In a medical observation system 1 of FIG. 1, instead of performing laparotomy on an abdominal wall as in the past, perforating tools referred to as trocars 25*a* and 25*b* are attached to several places of the abdominal wall. Then, a laparoscope (hereinafter, also referred to as endoscope) 11 as an observation medical apparatus for observing the inside of the body of a patient, an energy treatment tool 22, forceps 23, and the like are inserted into the body from the holes provided to the trocars 25*a* and 25*b*.

An operator performs treatment such as removal of an affected part U (tumor etc.) with the energy treatment tool 22 and the like while viewing in real time an image of the affected part U inside the body of the patient, the image being captured by the endoscope 11. The endoscope 11, the energy treatment tool 22, and the forceps 23 are held by the operator, a robot, or the like.

It should be noted that the operator refers to a health professional involved in a surgery performed in a surgery room. The operator includes members involved in the surgery, for example, in addition to a surgeon, assistants, scopists, and nurses of the surgery, doctors monitoring that surgery from another place different from the surgery room. In the example of FIG. 1, the endoscope 11 is held by, for example, a scopist. The endoscope 11 includes a camera head, the camera head including a scope to be inserted into a patient and an imaging device that receives light guided by the scope to perform imaging. It should be noted that the scope may of a hard type or a soft type. Further, the scope and the imaging device may be integrated.

In the surgery room where such an endoscopic surgery is performed, a cart 31 on which apparatuses for the endoscopic surgery are mounted, a patient bed 33 on which a patient lies, a foot switch 35, and the like are installed. For example, apparatuses such as a camera control unit (CCU) 13, a light source apparatus 17 (light source), an apparatus for surgical tools 21, a pneumoperitoneum apparatus 24, a display apparatus 15, a recorder 26, and a printer 27 are placed as medical apparatuses on the cart 31.

An image signal of the affected part U, which is captured through an observation optical system of the endoscope 11, is transmitted to the CCU 13 via a camera cable that is a signal transmission cable. The CCU 13 may be connected to the endoscope 11 via the camera cable, and may also be connected to the endoscope 11 via a wireless communication path. The CCU 13 performs signal processing on the image signal output from the endoscope 11 and outputs the image signal, on which the signal processing is performed, to the display apparatus 15. With such a configuration, a surgical field image of the affected part U is displayed on the display apparatus 15.

It should be noted that the CCU 13 outputs the image signal, on which the signal processing is performed, to the recorder 26, to cause the recorder 26 to record the surgical field image of the affected part U as image data (for example, data of moving image). Further, the CCU 13 outputs the image signal, on which the signal processing is performed, to the printer 27, to cause the printer 27 to print the surgical field image of the affected part U.

The light source apparatus 17 is connected to the endoscope 11 via a light guide cable and irradiates the affected part U with light of various wavelengths while switching. The light from the light source apparatus 17 may be used as auxiliary light, for example.

The apparatus for surgical tools 21 corresponds to, for example, a high-frequency output apparatus that outputs a high-frequency current to the energy treatment tool 22 that cuts the affected part U by using electrical heat.

The pneumoperitoneum apparatus 24 includes air-supply/intake means and supplies air to, for example, the abdomen region inside the body of the patient.

The foot switch 35 controls the CCU 13, the apparatus for surgical tools 21, and the like with a foot operation of an operator, an assistant, or the like as a trigger signal.

<Image Processing in Medical Observation System>

In the CCU 13 of the medical observation system having such a configuration, SLAM is performed on the basis of an image obtained by imaging a surgical field with the endoscope 11. By the SLAM, a three-dimensional map, i.e., three-dimensional information indicating the shape of a space including a surgical field inside the body of a patient is generated, and the position and the posture of the endoscope 11 at each timing are estimated. Three-dimensional information is information that includes three-dimensional coordinate information (for example, the three-dimensional map).

The estimation results of the position and the posture of the endoscope 11, which are obtained by the SLAM, are used for controlling the direction of the image, for example, when an image of an organ or the like, which is separately obtained by computed tomography (CT), magnetic resonance imaging (MRI), or the like, is displayed. The image of the organ, which is obtained by CT or the like, is displayed on the display apparatus 15 in a direction corresponding to the position and the posture of the endoscope 11.

The SLAM in the CCU 13 is performed, for example, on the basis of a special light image, which is an image captured with the surgical field being irradiated with special light. Since the SLAM is performed on the basis of the special light image captured during irradiation with special light, such SLAM can be called special light SLAM. It should be noted that the algorithm of the SLAM based on images only needs to be an algorithm capable of generating a three-dimensional map and a self-position and a self-posture on the three-dimensional map on the basis of a feature value in the image, and an existing algorithm may be employed. For example, an algorithm such as machine learning SLAM, which generates a three-dimensional map and estimates a self-position by using parallel tracking and mapping (PTAM), dense tracking and mapping (DTAM), Oriented FAST and Rotated BREIF (ORB)-SLAM, or machine learning using a multi-layer neural network, may be employed. Further, not only the image but also the information of an inertial measurement unit (IMU) sensor or a depth sensor may be combined.

Figure 2:
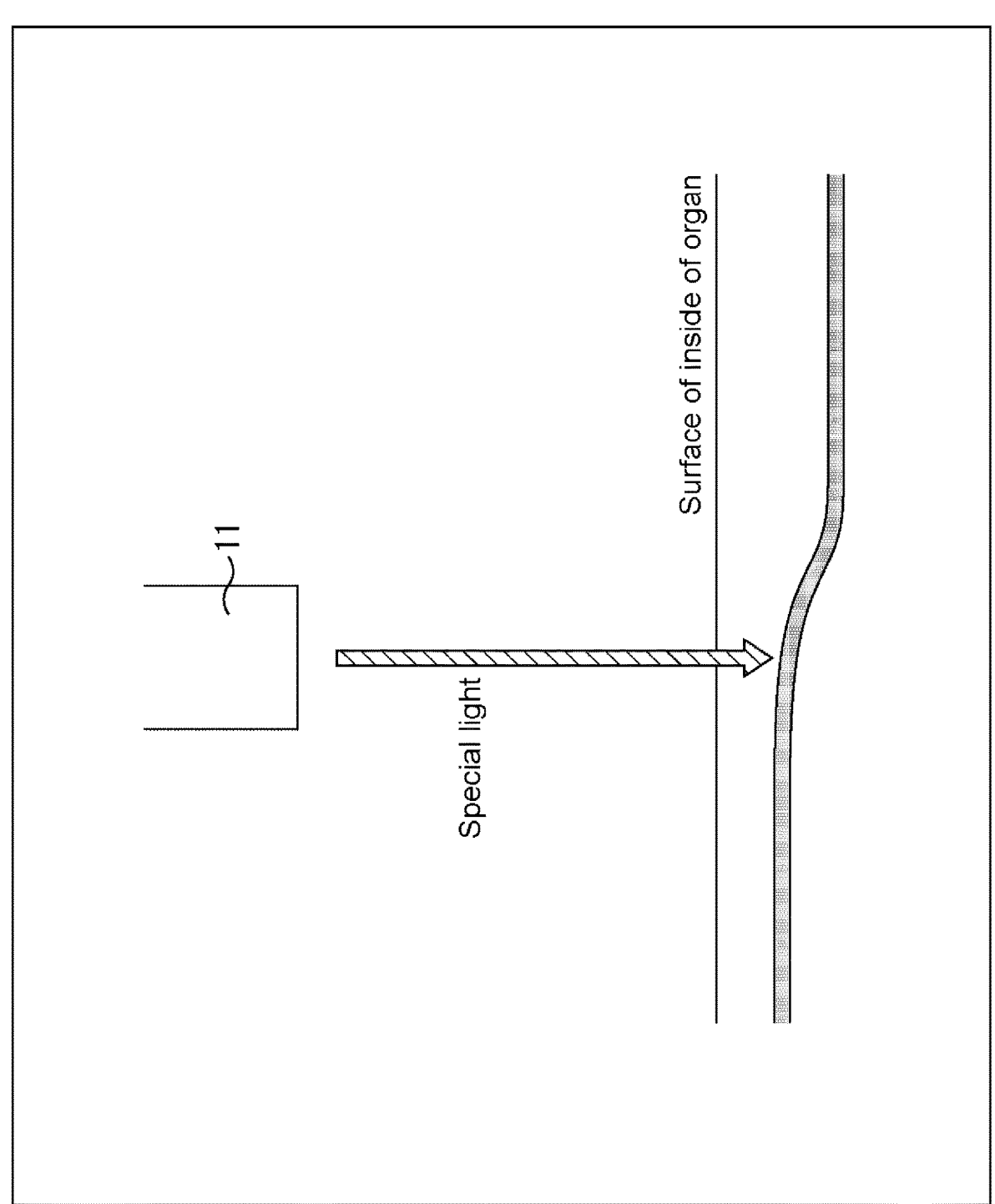
FIG. 2 is a diagram showing an example of irradiation with special light.

FIG. 2 is a diagram showing an example of irradiation with special light.

The surgical field is irradiated with special light of the light source apparatus 17, as a light source, from the tip of the endoscope 11 as indicated by the arrow of FIG. 2, and imaging is performed in this state.

If infrared (IR) light is used as the special light, as indicated by the arrow of FIG. 2, the special light is not reflected on the surface of the surgical field. The special light reaches a predetermined structure at a deep part, such as a blood vessel, and is reflected on the structure at the deep part. The structure at the deep part, which does not appear (is difficult to appear) in a visible light image captured by irradiation with visible light, appears with emphasis in a special light image. It should be noted that, for example, the IR light is Near IR light and has the wavelength band with a peak wavelength of 760-800 nm.

In the CCU 13, the SLAM is performed on the basis of the special light image, and a three-dimensional map is generated, in which the edge of the structure at the deep part, and the like are used as feature points. Further, using the three-dimensional map thus generated, the position and the posture are estimated.

The surface shape of the surgical field is changed by treatment such as excision of a lesioned part during a surgery, whereas the blood vessel at the deep part or the like is basically preserved and does not change. When the SLAM based on the special light image is performed, a three-dimensional map can be generated on the basis of the feature points less affected by the change of the surgical field, and SLAM results with high reliability can be obtained.

It should be noted that various types of light of wavelength bands (first wavelength band) different from the wavelength band (second wavelength band) of the visible light are used for the special light. Details of the special light will be described later.

<<Special Light SLAM>>

Example of Performing Special Light Observation

Functional Configuration of CCU

Figure 3:
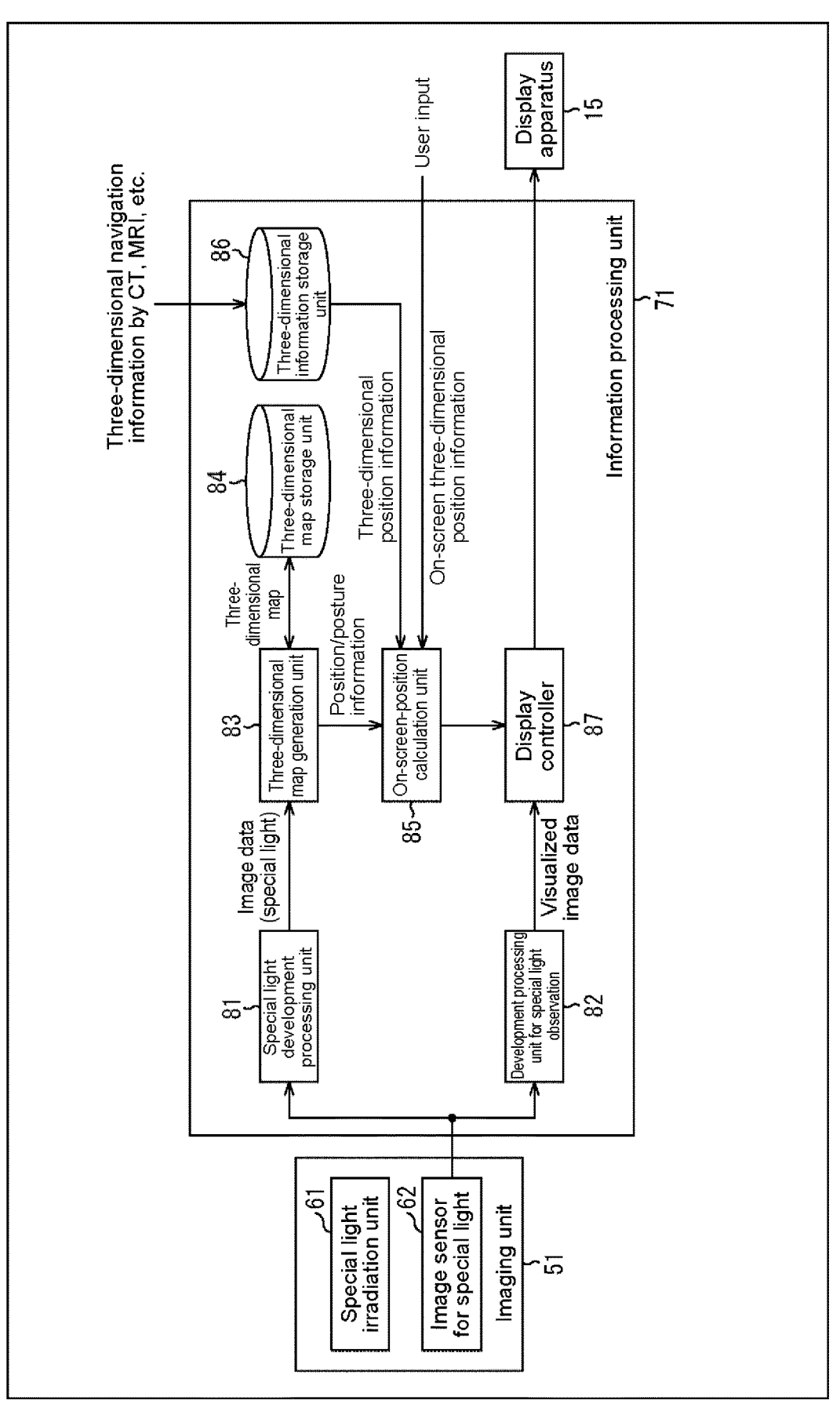
FIG. 3 is a block diagram showing a functional configuration example of a camera control unit (CCU).

FIG. 3 is a block diagram showing a functional configuration example of the CCU 13.

As shown in FIG. 3, an information processing unit 71 is achieved in the CCU 13. The information processing unit 71 is achieved when, for example, the central processing unit (CPU) constituting the CCU 13 executes a predetermined program stored a memory. In other words, the function of the CCU 13 is realized by a control processing circuit. The control processing circuit is, for example, circuitry including the CPU and the memory.

The information processing unit 71 includes a special light development processing unit 81, a development processing unit for special light observation 82, a three-dimensional map generation unit 83, a three-dimensional map storage unit 84, an onscreen-position calculation unit 85, a three-dimensional information storage unit 86, and a display controller 87.

An image signal output from an image sensor for special light 62 constituting an imaging unit 51 (image capture device) of the endoscope 11 (medical imaging device) is input to the special light development processing unit 81 and the development processing unit for special light observation 82. The imaging unit 51 includes a special light irradiation unit 61 and the image sensor for special light 62. The special light irradiation unit 61 irradiates the surgical field with special light. The image sensor for special light 62 images the surgical field during irradiation with special light.

The special light development processing unit 81 generates an RGB image, as a special light image, on the basis of raw signals supplied from the image sensor for special light 62, and outputs data of the special light image to the three-dimensional map generation unit 83.

The development processing unit for special light observation 82 generates an observation image, which visualizes the state of the surgical field, on the basis of raw signals supplied from the image sensor for special light 62. In the observation image, the state of the surgical field appears in a viewable manner. In the example of FIG. 3, the special light is used as observation light. Data of the observation image, which is generated by the development processing unit for special light observation 82, is supplied to the display controller 87.

The three-dimensional map generation unit 83 performs the special light SLAM, which is based on the special light image. For example, the surgical field being irradiated with the special light is repeatedly imaged. The special light SLAM by the three-dimensional map generation unit 83 is performed using the special light image sequentially supplied from the special light development processing unit 81.

The three-dimensional map generation unit 83 analyzes the special light image to set a point having a predetermined feature value to be a feature point, thus generating a three-dimensional map including such feature points. The three-dimensional map generation unit 83 outputs the generated three-dimensional map to the three-dimensional map storage unit 84 and causes the three-dimensional map storage unit 84 to store it. The three-dimensional map stored in the three-dimensional map storage unit 84 is sequentially updated in accordance with the processing by the three-dimensional map generation unit 83.

Further, the three-dimensional map generation unit 83 estimates the position and the posture of the endoscope 11 on the basis of the three-dimensional map or the like stored in the three-dimensional map storage unit 84 and outputs position/posture information, which indicates estimation results of the position and the posture, to the onscreen-position calculation unit 85.

The on-screen-position calculation unit 85 reads a three-dimensional image of an organ, which is generated in advance by using CT, MRI, or the like before a surgery, from the three-dimensional information storage unit 86 to acquire the three-dimensional image. Further, the on-screen-position calculation unit 85 acquires three-dimensional position information corresponding to navigation information input to the three-dimensional information storage unit 86 or three-dimensional position information that is input, for example, specified on the screen by an operator as a user.

The on-screen-position calculation unit 85 calculates the position and the posture of the endoscope 11, which are indicated by the position/posture information supplied from the three-dimensional map generation unit 83, and the direction of the three-dimensional image, which corresponds to the position or the like indicated by the three-dimensional position information. The on-screen-position calculation unit 85 converts the three-dimensional image so as to be viewed in accordance with the calculated direction, and outputs the converted three-dimensional image to the display controller 87. The calculating the direction of the three-dimensional image indicates calculating a rotation of the three-dimensional image. The converted three-dimensional image is a two-dimensional image of the three-dimensional image as viewed from the predetermined direction.

The display controller 87 synthesizes the converted three-dimensional image by the on-screen-position calculation unit 85 with the observation image whose data is supplied from the development processing unit for special light observation 82, and causes the display apparatus 15 to display the synthesized observation image.

Example of Special Light

Here, the special light used for capturing a special light image will be described.

(1) Case of Using IR Light (Infrared Ray)

If light such as IR light, with which a blood vessel structure at a deep part can be observed, is used as the special light, a three-dimensional map free from the influence of the change in state of the surface can be obtained. In other words, SLAM less affected by the treatment in a surgery is achieved. Like the IR light, the light having a longer wavelength than the wavelength of the visible light can be used as the special light. In this case, the wavelength band of the special light is larger than the wavelength band of the visible light.

(2) Case of Using Bluish Light

If bluish light, with which superficial blood vessels can be emphasized for observation, is used as the special light, the feature points of the SLAM are set for the blood vessels and the like appearing in a special light image. Since the blood vessels are basically preserved in the surgery, SLAM less affected by the treatment in the surgery is achieved.

(3) Case of Using Light with High Transmissivity

If light with high transmissivity, which is higher than the transmissivity of visible light, is used as the special light, a special light image in which the surgical field vividly appears can be obtained even if mist or haze occurs within the organ. Since a feature point can be obtained on the basis of the special light image, the interrupt of the SLAM can be suppressed. Depending on the details of the treatment, mist or the like occurs within the organ, and the SLAM is difficult to be continued in some cases when a visible light image is used. This can be prevented from occurring.

(4) Case of Using Polarized Light as Special Light

If polarized light is used as the special light, a feature point in a specular reflection region can be obtained from a special light image. This allows SLAM to be performed including the specular reflection region. During a surgery, for example, an organ has fluid, and a region where specular reflection is caused may be formed in a surgical field. If a visible light image is used, a feature point in the specular reflection region is difficult to detect in some cases. Such a case can be prevented from occurring by using the special light image.

The polarized light that is the special light is generated by, for example, using a polarization filter. Visible light emitted from a light source passes through the polarization filter, and polarized light is thus generated.

(5) Case of Using Light Forming Known Space Pattern as Special Light

Light (structured light), which projects a known space pattern such as a checker pattern or a dot pattern, can be used as the special light. In this case, a three-dimensional shape of the surgical field can be more correctly detected.

(6) Case of Using Pulse-Modulated Light as Special Light

If pulse-modulated light is used as the special light, a distance to the surgical field can be directly measured on the basis of the phase difference between reflection light and irradiation light. A three-dimensional map is generated on the basis of the measurement result of the distance to each position.

As described above, various types of light of wavelength bands different from the wavelength band of visible light can be used as the special light.

It should be noted that the visible light is white light and has the wavelength band, for example, from a predetermined wavelength whose lower limit falls in the range of substantially 360 to 400 nm to a predetermined wavelength whose upper limit falls in the range of substantially 760 to 830 nm. Various types of light of wavelength bands different from the wavelength band of such visible light can be used as the special light.

It may also be possible to use not the light of the wavelength band different from those of the visible light as the special light, but light whose type of the light source (LED, laser, etc.) is different from that of the visible light as the special light. Alternatively, it may also be possible to use light whose irradiation strength is different from that of the visible light as the special light. It may also be possible to use, as the special light, light for emitting a space pattern different from the space pattern emitted using the visible light.

Operation of CCU

Here, the surgical-field-image display processing of the CCU 13 will be described with reference to the flowchart of FIG. 4.

In Step S1, the special light irradiation unit 61 of the imaging unit 51 irradiates the surgical field with the special light.

In Step S2, the image sensor for special light 62 images the surgical field during the irradiation with the special light.

In Step S3, the special light development processing unit 81 of the information processing unit 71 generates a special light image on the basis of the raw signals supplied from the image sensor for special light 62.

In Step S4, the development processing unit for special light observation 82 generates an observation image on the basis of the raw signals supplied from the image sensor for special light 62. This observation image may be the same as the special light image of S2, or it may be a different special light image.

In Step S5, the three-dimensional map generation unit 83 analyzes the special light image supplied from the special light development processing unit 81 to generate a three-dimensional map.

In Step S6, the three-dimensional map generation unit 83 estimates a position and a posture of the endoscope 11 on the basis of the three-dimensional map.

In Step S7, the on-screen-position calculation unit 85 converts the direction of the three-dimensional image on the basis of estimation results of the position and the posture by the three-dimensional map generation unit 83.

In Step S8, the display controller 87 synthesizes the converted three-dimensional image, which is supplied from the on-screen-position calculation unit 85, with the observation image, which is supplied from the development processing unit for special light observation 82.

In Step S9, the display controller 87 causes the display apparatus 15 to display the synthesized observation image.

By the special light SLAM, which is the SLAM based on the special light image as described above, highly reliable SLAM results can be obtained.

Example of Performing Visible Light Observation

The observation image may be generated on the basis of the image signal, which is obtained by receiving reflection light of the visible light. In this example, the visible light is used as observation light.

Figure 5:
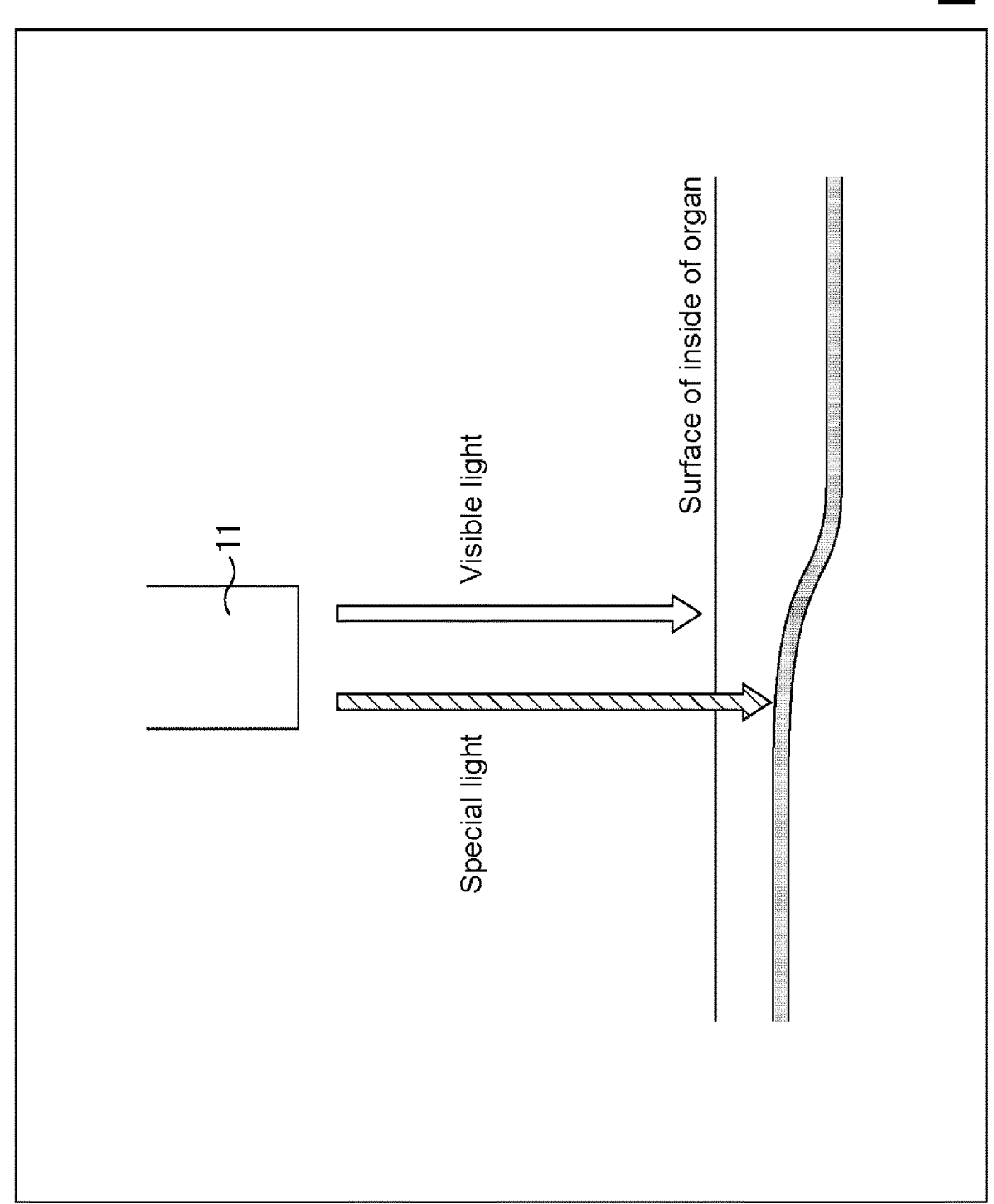
FIG. 5 is a diagram showing an example of irradiation with special light and visible light.

FIG. 5 is a diagram showing an example of the irradiation with the special light and the visible light.

If the visible light is used as the observation light, as shown in FIG. 5, the surgical field is irradiated with the special light and the visible light from the tip of the endoscope 11, and imaging is performed in this state. A special light image obtained by receiving reflection light of the special light is used for the SLAM as described above, and a visible light image obtained by receiving reflection light of the visible light is used as an observation image.

Functional Configuration of CCU

Figure 6:
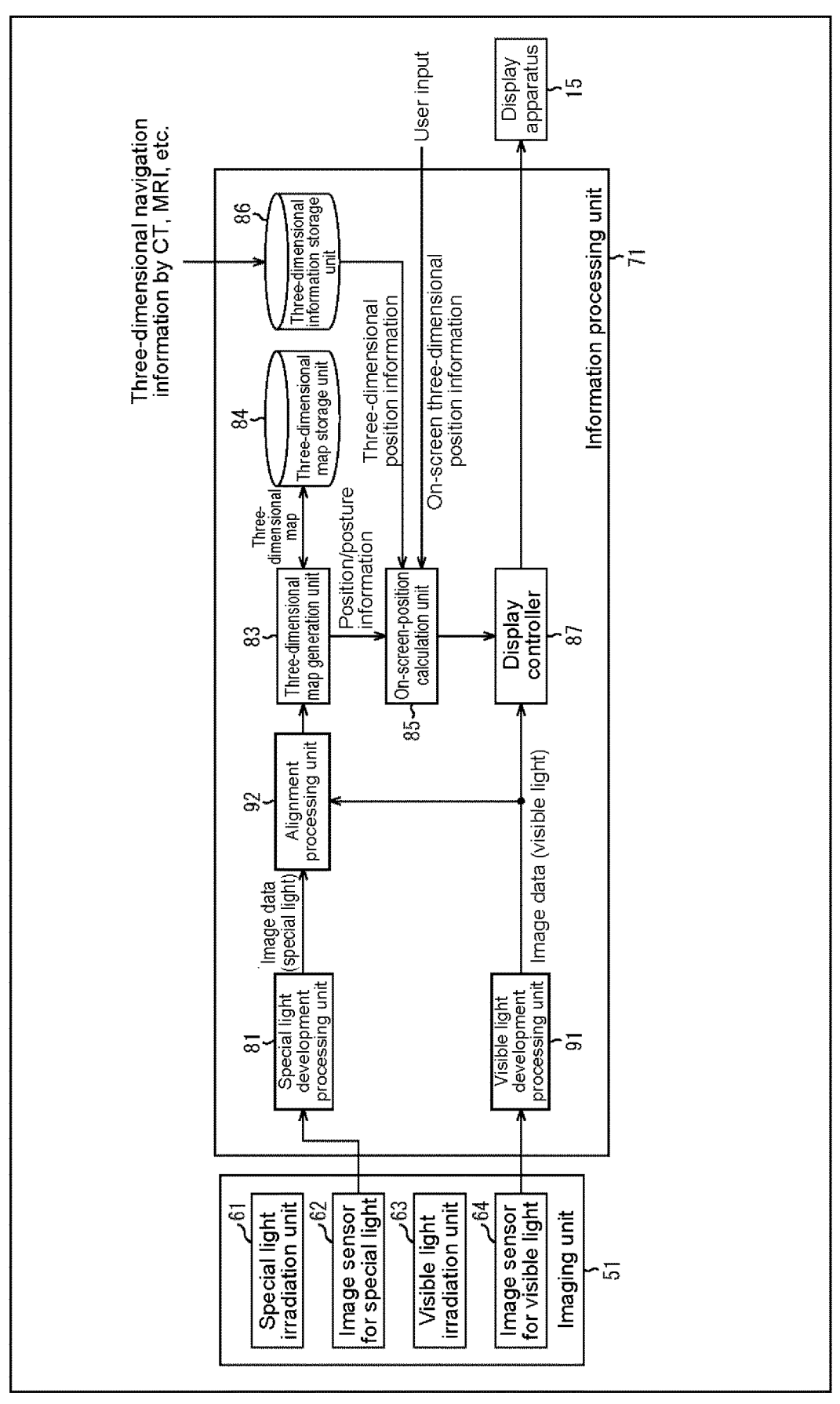
FIG. 6 is a block diagram showing another functional configuration example of the CCU.

FIG. 6 is a block diagram showing another functional configuration example of the CCU 13.

In the configurations shown in FIG. 6, the same configurations as those described with reference to FIG. 3 are denoted by the same reference symbols. Overlapping description will be appropriately omitted.

The configuration of the information processing unit 71 shown in FIG. 6 is different from the configuration shown in FIG. 3 in that a visible light development processing unit 91 is provided instead of the development processing unit for special light observation 82, and an alignment processing unit 92 is additionally provided.

The imaging unit 51 includes, in addition to the special light irradiation unit 61 and the image sensor for special light 62, a visible light irradiation unit 63 and an image sensor for visible light 64. The visible light irradiation unit 63 irradiates the surgical field with visible light. The image sensor for visible light 64 images the surgical field during irradiation with visible light. The irradiation with the special light by the special light irradiation unit 61 and the irradiation with the visible light by the visible light irradiation unit 63 are, for example, simultaneously performed. The irradiation with the special light by the special light irradiation unit 61 and the irradiation with the visible light by the visible light irradiation unit 63 may be performed in a time division manner.

Figure 7:
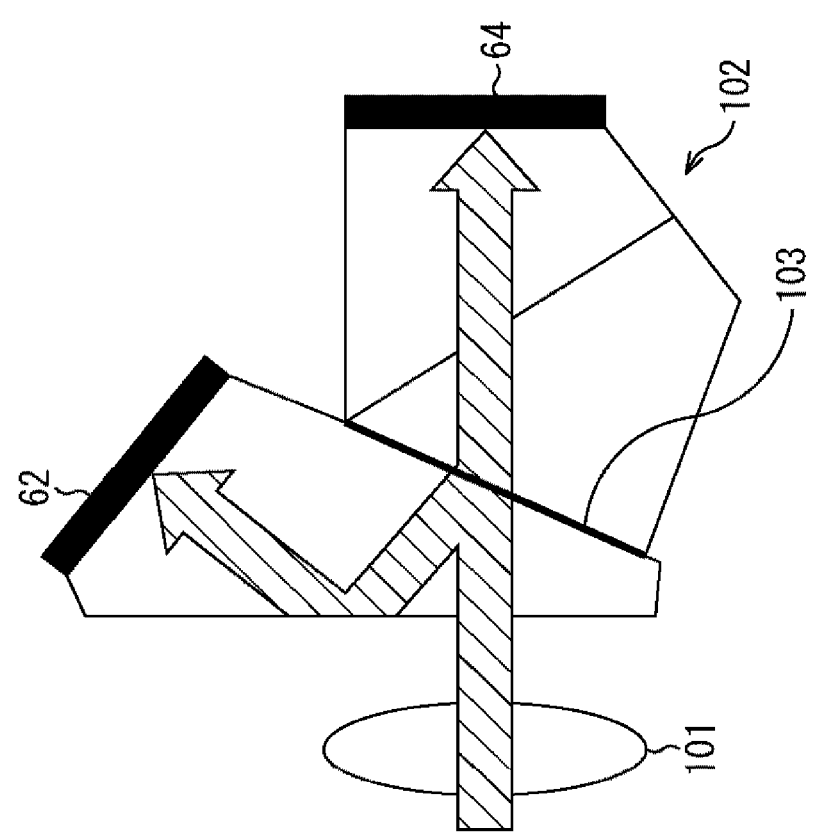
FIG. 7 is a diagram showing a configuration example of a prism and a dichroic mirror.

A prism 102 and a dichroic mirror 103 as shown in FIG. 7 are provided in front of the image sensor for special light 62 and the image sensor for visible light 64. In the light passing through a lens 101 provided to the scope of the endoscope 11, the special light is reflected on the dichroic mirror 103 and guided to the image sensor for special light 62. Further, in the light passing through the lens 101, the visible light passes through the dichroic mirror 103 and is guided to the image sensor for visible light 64.

As shown in FIG. 6, the image signal output from the image sensor for special light 62 is input to the special light development processing unit 81, and the image signal output from the image sensor for visible light 64 is input to the visible light development processing unit 91.

The visible light development processing unit 91 generates a visible light image on the basis of the raw signals supplied from the image sensor for visible light 64 and outputs the visible light image as an observation image indicating the state of the surgical field. Data of the visible light image output from the visible light development processing unit 91 is supplied to the display controller 87 and the alignment processing unit 92.

The alignment processing unit 92 performs alignment, in which the position of each pixel of the special light image supplied from the special light development processing unit 81 is electronically aligned with the position of each pixel of the visible light image supplied from the visible light development processing unit 91. The alignment processing unit 92 outputs the special light image obtained after the alignment to the three-dimensional map generation unit 83.

The display controller 87 synthesizes the converted three-dimensional image by the on-screen-position calculation unit 85 with the visible light image whose data is supplied from the visible light development processing unit 91, and causes the display apparatus 15 to display the synthesized visible light image.

Operation of CCU

Here, the surgical-field-image display processing of the CCU 13 having the configuration of FIG. 6 will be described with reference to the flowchart of FIG. 8.

In Step S21, the special light irradiation unit 61 of the imaging unit 51 irradiates the surgical field with the special light. Further, the visible light irradiation unit 63 irradiates the surgical field with the visible light.

In Step S22, the image sensor for special light 62 images the surgical field during the irradiation with the special light. Further, the image sensor for visible light 64 images the surgical field during the irradiation with the visible light.

In Step S23, the special light development processing unit 81 of the information processing unit 71 generates a special light image on the basis of the raw signals supplied from the image sensor for special light 62.

In Step S24, the visible light development processing unit 91 generates an observation image (visible light image) on the basis of the raw signals supplied from the image sensor for visible light 64.

In Step S25, the alignment processing unit 92 performs alignment on the basis of the special light image, which is supplied from the special light development processing unit 81, and the visible light image, which is supplied as an observation image from the visible light development processing unit 91.

In Step S26, the three-dimensional map generation unit 83 analyzes the special light image supplied from the alignment processing unit 92 to generate a three-dimensional map.

In Step S27, the three-dimensional map generation unit 83 estimates a position and a posture of the endoscope 11 on the basis of the three-dimensional map.

In Step S28, the on-screen-position calculation unit 85 converts the direction of the three-dimensional image on the basis of estimation results of the position and the posture by the three-dimensional map generation unit 83.

In Step S29, the display controller 87 synthesizes the converted three-dimensional image, which is supplied from the on-screen-position calculation unit 85, with the observation image, which is supplied from the visible light development processing unit 91.

In Step S30, the display controller 87 causes the display apparatus 15 to display the synthesized observation image.

As described above, providing the visible light irradiation unit 63 and the image sensor for visible light 64 to the imaging unit 51 allows the use of the visible light image as the observation image.

<<Combination SLAM>>

The generation of the three-dimensional map and the estimation of the position and the posture may be performed by using in combination the special light SLAM, which is the SLAM using the special light image, and the visible light SLAM, which is the SLAM using the visible light image. The SLAM using in combination the special light SLAM and the visible light SLAM is the combination SLAM.

Figure 9:
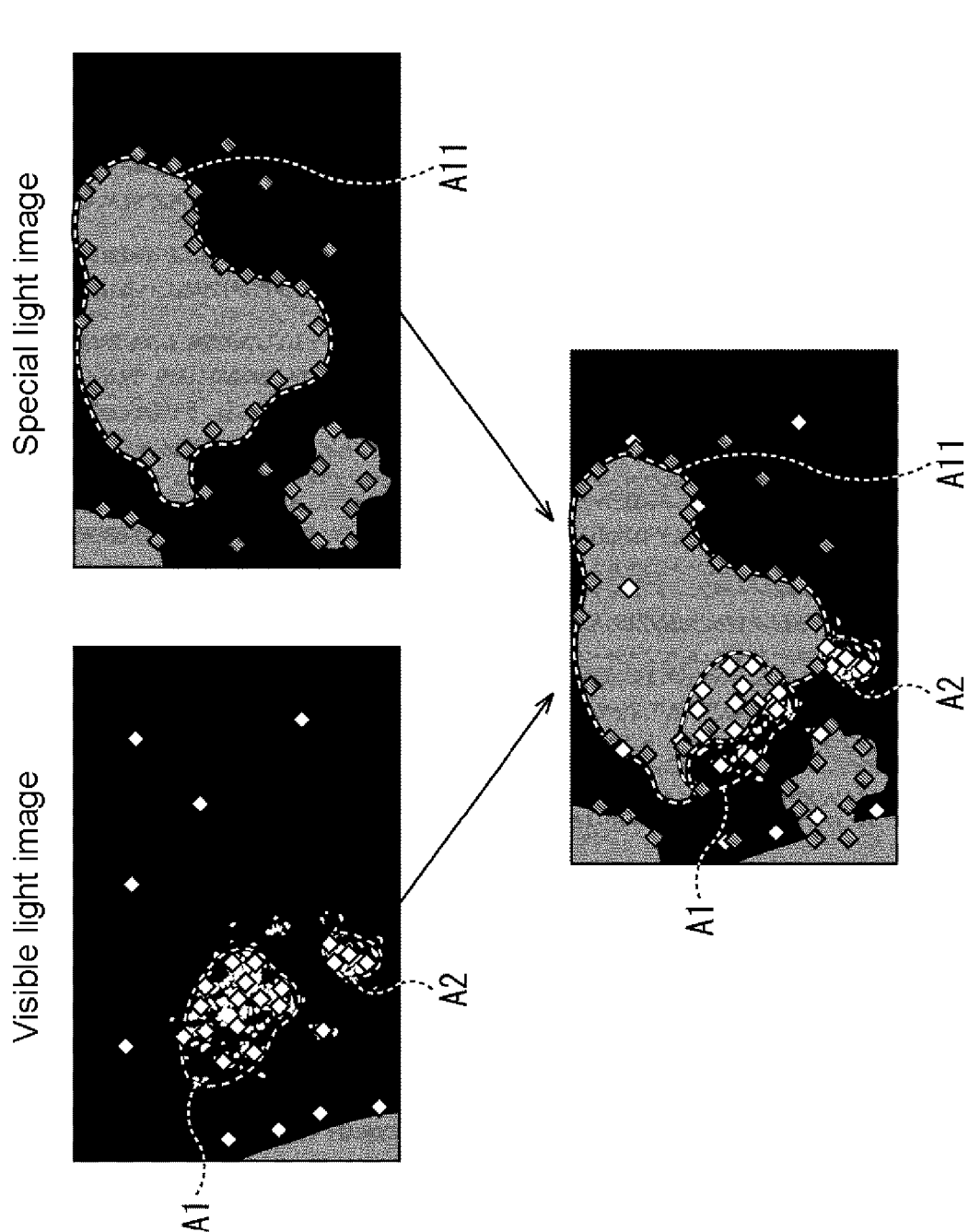
FIG. 9 is a diagram showing an example of combination SLAM.

FIG. 9 is a diagram showing an example of the combination SLAM.

The image on the left in the upper row of FIG. 9 is a visible light image, and the image on the right therein is a special light image. The visible light image and the special light image shown in FIG. 9 are images each obtained by imaging the same range. Further, rhombuses shown in the images are each a feature point detected by analyzing the images. Details appearing in the images are different depending on the wavelength of the light used for each imaging, and the feature points are set at different positions accordingly.

In the visible light image of FIG. 9, regions A1 and A2 surrounded by the broken lines are regions where specular reflection is caused by the emitted visible light. The regions A1 and A2 appear as bright spots in the visible light image. In this example, many feature points are set at the positions of the respective bright spots.

Meanwhile, in the special light image of FIG. 9, a region A11 surrounded by the broken line is a region where a blood vessel structure at a deep part appears. In this example, many feature points are set in the vicinity of the edge of the blood vessel structure.

The combination SLAM is the SLAM using the feature points detected from the visible light image and the feature points detected from the special light image, as indicated by the points of the arrows of FIG. 9. The position and posture of the endoscope 11 when the visible light image is captured, and the position and posture of the endoscope 11 when the special light image is captured are the same, and thus the feature points detected from two or more images can be easily superimposed on the same coordinate system.

The feature points detected from the visible light image and the feature points detected from the special light image are different from each other in position, and thus the combination SLAM allows a more robust three-dimensional map to be generated.

In the combination SLAM, all of the feature points detected from the visible light image and the feature points detected from the special light image are not used, and the feature points with high reliability are used.

The three-dimensional map may be generated on the basis of the feature points with high reliability, or the position and the posture may be estimated on the basis of the feature points with high reliability among the feature points constituting the three-dimensional map.

In the latter case, for example, a three-dimensional map including the feature points on the visible light image, and a three-dimensional map including the feature points on the special light image are generated, and the two three-dimensional maps are synthesized, to generate a three-dimensional map of the combination SLAM. Among the feature points constituting the three-dimensional map of the combination SLAM, the feature points with high reliability are used for estimation of the position and the posture.

Functional Configuration of CCU

Figure 10:
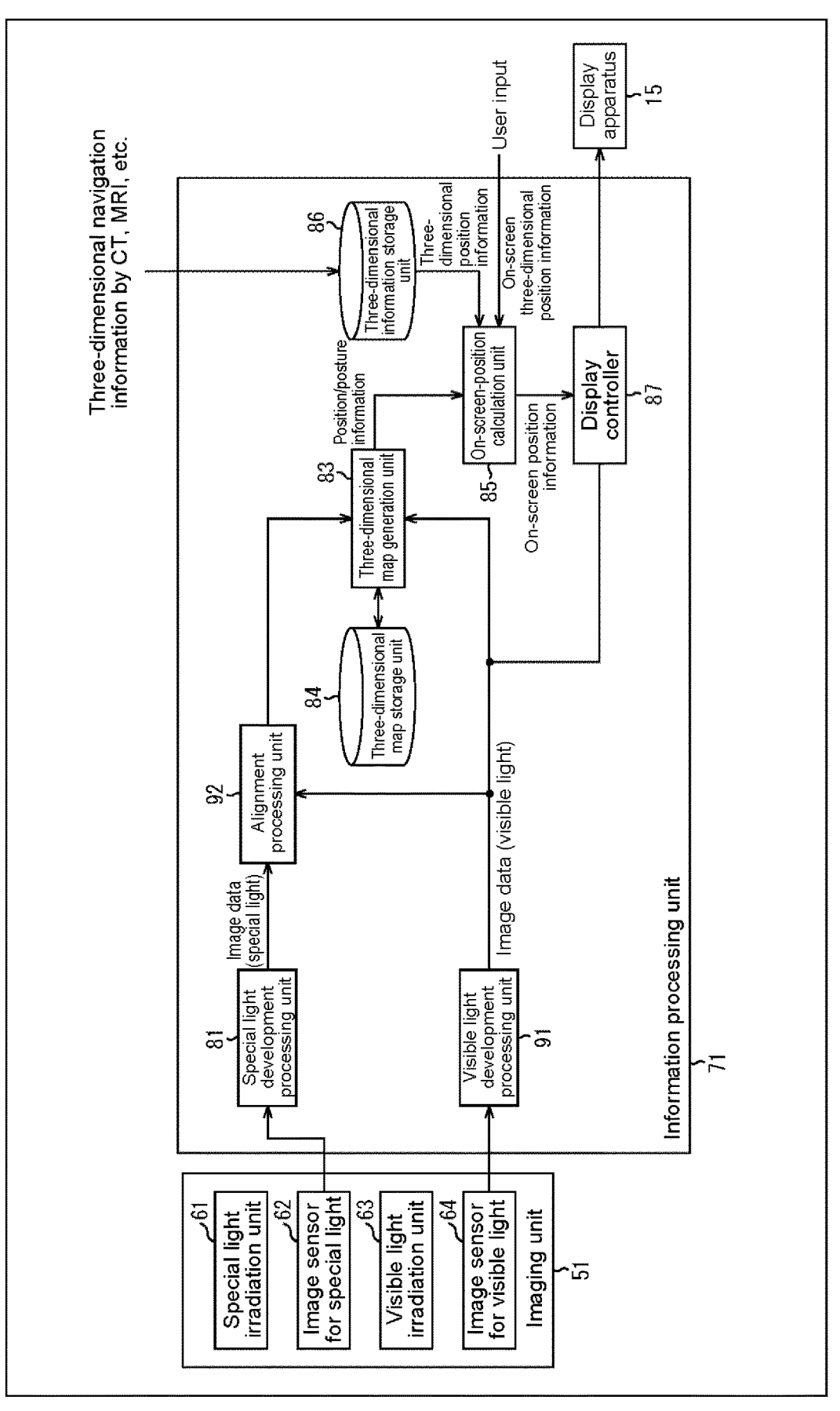
FIG. 10 is a block diagram showing still another functional configuration example of the CCU.

FIG. 10 is a block diagram showing still another functional configuration example of the CCU 13.

In the configurations shown in FIG. 10, the same configurations as those described with reference to FIG. 6 are denoted by the same reference symbols. Overlapping description will be appropriately omitted.

The three-dimensional map generation unit 83 acquires the special light image obtained after the alignment, which is supplied from the alignment processing unit 92, and the visible light image supplied from the visible light development processing unit 91. The three-dimensional map generation unit 83 detects feature points on the special light image and feature points on the visible light image and generates a three-dimensional map on the basis of the detected feature points.

For example, the three-dimensional map generation unit 83 calculates the reliability of the feature points on the special light image and the reliability of the feature points on the visible light image and generates a three-dimensional map including the feature points with high reliability.

The calculation for the reliability is performed as follows, for example: the difference in feature value between a feature point detected from a certain frame and a corresponding feature point detected from the frame one frame before is calculated; and on the basis of the difference, as the difference in feature value becomes smaller, a higher value is set for the reliability, and as the difference in feature value becomes larger, a lower value is set for the reliability.

For example, in a case where both of the feature point detected from the special light image and the feature point detected from the visible light image are included in a predetermined range (in a case where both of the feature points are at near positions), the three-dimensional map generation unit 83 selects the feature point with a higher reliability as a feature point constituting the three-dimensional map. For the method of selecting a feature point constituting the three-dimensional map, various methods as will be described later can be employed.

The three-dimensional map generation unit 83 estimates the position and the posture of the endoscope 11 on the basis of the three-dimensional map including the selected feature points as described above and outputs the position/posture information to the on-screen-position calculation unit 85.

The on-screen-position calculation unit 85 calculates the direction of the three-dimensional image on the basis of the position, the posture, and the like of the endoscope 11, which are indicated by the position/posture information supplied from the three-dimensional map generation unit 83. The on-screen-position calculation unit 85 converts the three-dimensional image so as to be seen in accordance with the calculated direction and outputs the converted three-dimensional image to the display controller 87.

The display controller 87 synthesizes the three-dimensional image, which is converted by the on-screen-position calculation unit 85, with the visible light image whose data is supplied from the visible light development processing unit 91, and then causes the display apparatus 15 to display the synthesized visible light image.

In the case where the three-dimensional map including the feature points of the visible light image and the three-dimensional map including the feature points of the special light image are generated, the former three-dimensional map may be displayed by the display controller 87. For example, such a display that superimposes the information of a blood vessel detected from the special light image on the three-dimensional map including the feature points of the visible light image can be performed.

Operation of CCU

Figure 11:
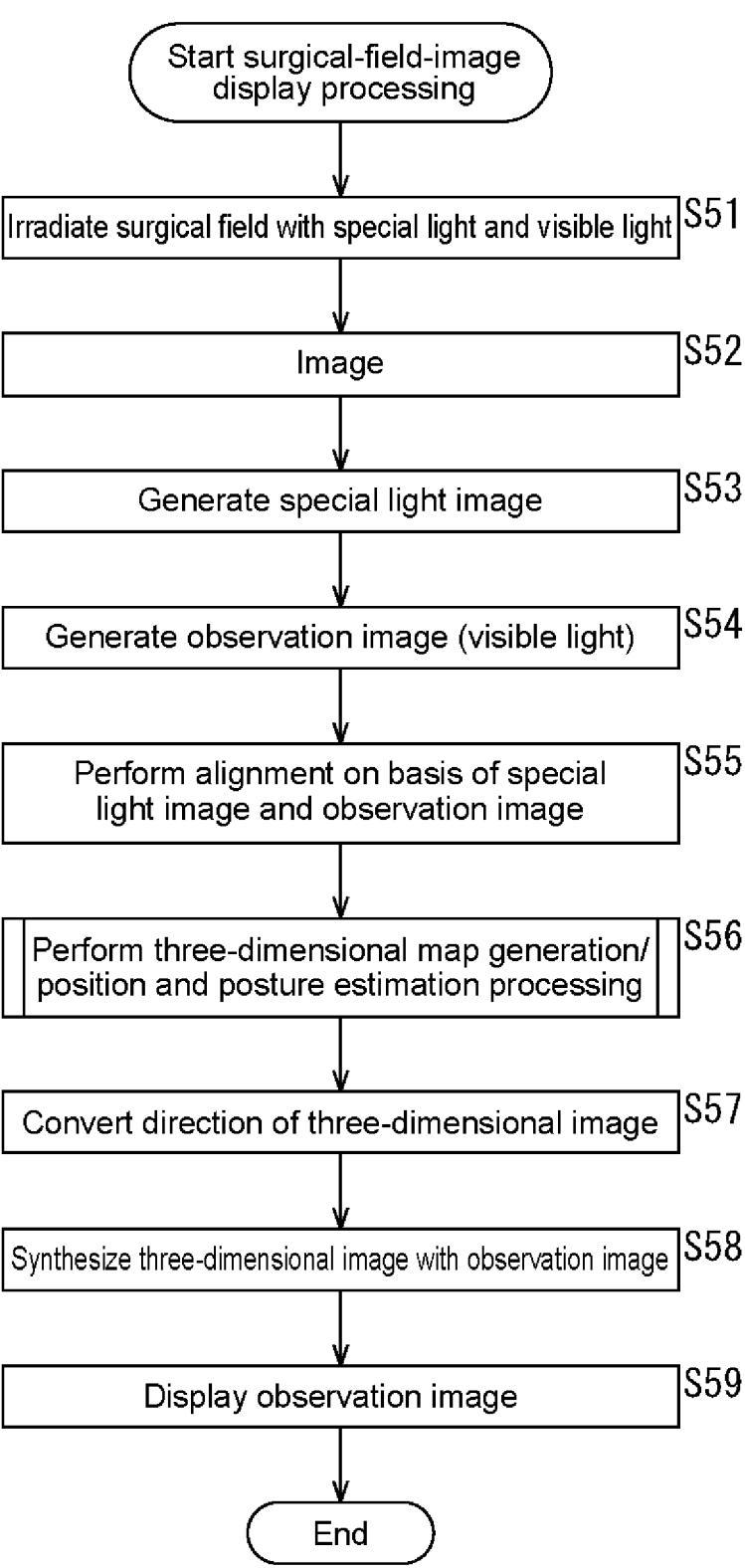
FIG. 11 is a flowchart for describing surgical-field-image display processing.

Here, the surgical-field-image display processing of the CCU 13 having the configuration of FIG. 10 will be described with reference to the flowchart of FIG. 11.

Figure 8:
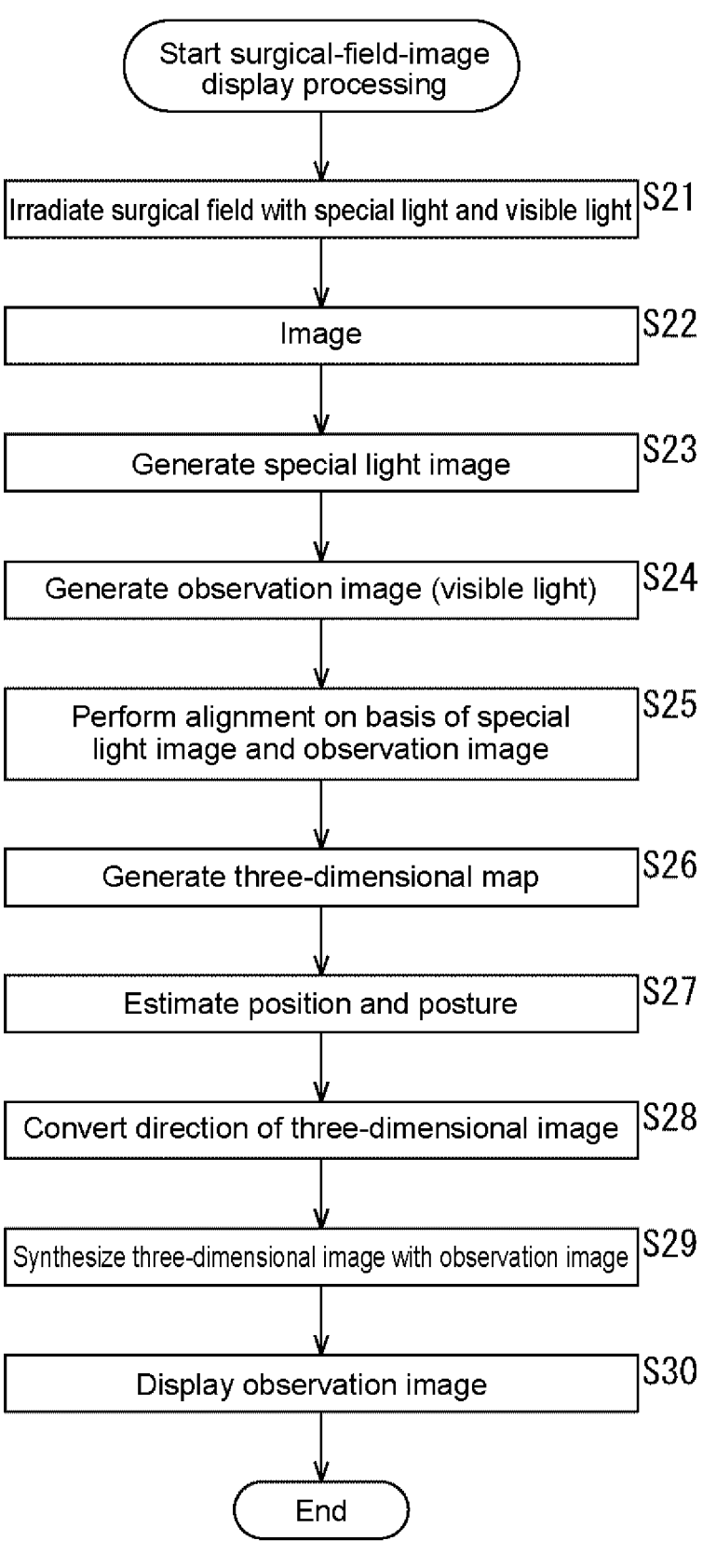
FIG. 8 is a flowchart for describing surgical-field-image display processing.

The processing from Steps S51 to S55 is processing similar to the processing from Steps S21 to S25 of FIG. 8. The special light image obtained after the alignment and the visible light image captured during the irradiation with visible light are supplied to the three-dimensional map generation unit 83.

In Step S56, the three-dimensional map generation unit 83 performs three-dimensional map generation/position and posture estimation processing. The three-dimensional map generation/position and posture estimation processing performed herein is the processing for the combination SLAM. Details of the three-dimensional map generation/position and posture estimation processing will be described later.

The processing from Steps S57 to S59 is processing similar to the processing from Steps S28 to S30 of FIG. 8. The synthesis for the three-dimensional image is performed using the estimation results of the position and the posture by the three-dimensional map generation/position and posture estimation processing, and the visible light image obtained after the synthesis of the three-dimensional image is displayed.

Three-Dimensional Map Generation/Position and Posture Estimation Processing

Figure 12:
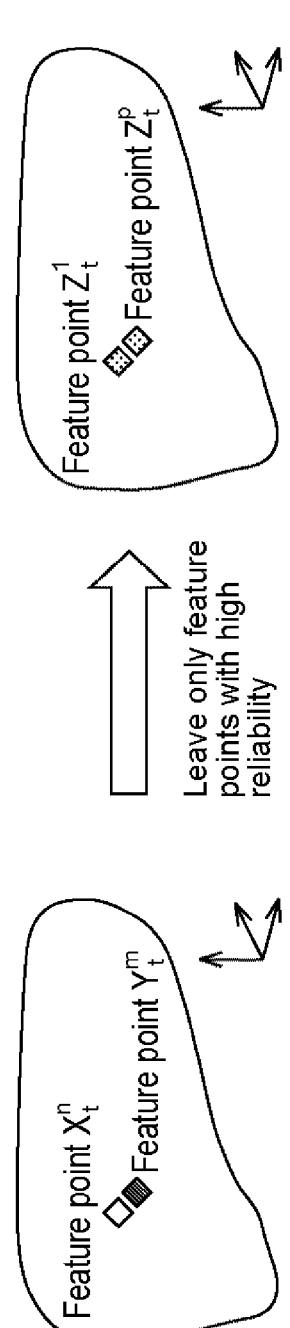
FIG. 12 is a diagram showing an example of the feature points used for three-dimensional map generation/position and posture estimation processing.

FIG. 12 is a diagram showing an example of the feature points used for the three-dimensional map generation/position and posture estimation processing.

As shown in FIG. 12, in the three-dimensional map generation/position and posture estimation processing, a three-dimensional map is generated such that the feature points with high reliability are left among a feature point $X''_t$ detected from the visible light image and a feature point $Y'''_t$ detected from the special light image at a certain time t. The three-dimensional map includes feature points $Z^1_t, \ldots, Z^P_t$, which are left as the feature points with high reliability.

Figure 13:
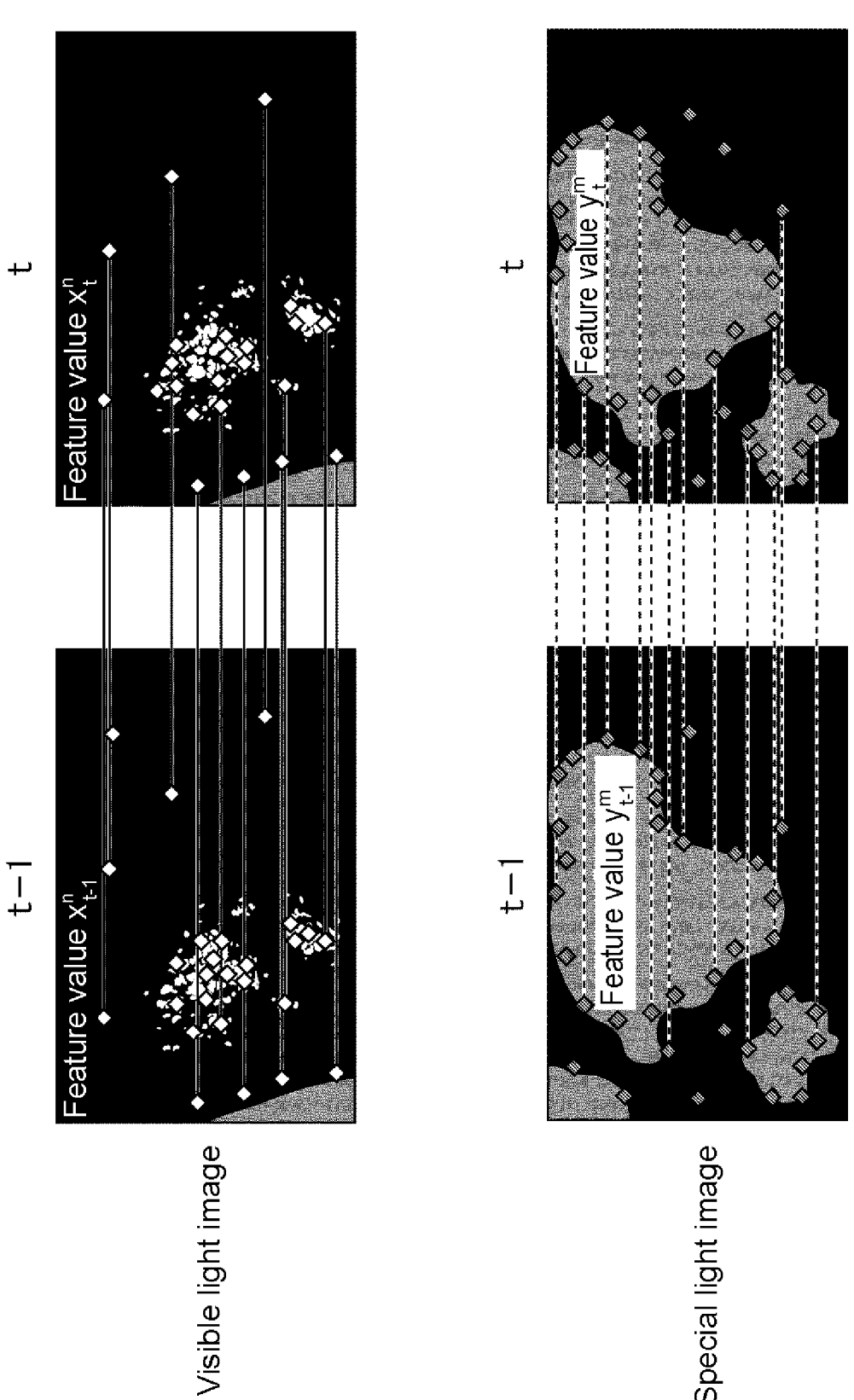
FIG. 13 is a diagram showing an example of the feature points detected from a visible light image and the feature points detected from a special light image.

FIG. 13 is a diagram showing an example of the feature points detected from the visible light image and the feature points detected from the special light image.

The upper row of FIG. 13 shows the feature points detected from the visible light image. The lower row of FIG. 13 shows the feature points detected from the special light image.

As shown in the visible light image on the right, the feature value of the feature point $X''_t$ detected from the visible light image of the frame at a time t (visible light image of t-th frame) is represented by a feature value $x''_t$. Further, as shown in the visible light image on the left, the feature value of the feature point $X''_{t-1}$ detected from the visible light image of the frame at a time t–1 (visible light image of (t–1)-th frame) is represented by a feature value $x''_{t-1}$.

The reliability of each feature point $X''_t$ detected from the visible light image is calculated on the basis of the feature value $x''_t$ and the feature value $x''_{t-1}$, which is a feature value of a corresponding feature point $X''_{t-1}$ of the frame one frame before, as indicated by being connected to each other using the horizontal lines.

Similarly, as shown in the special light image on the right, the feature value of the feature point $Y'''_t$ detected from the special light image of the t-th frame is represented by a feature value $y'''_t$. Further, as shown in the special light image on the left, the feature value of the feature point $Y'''_{t-1}$ detected from the special light image of the (t–1)-th frame) is represented by a feature value $y'''_{t-1}$.

The reliability of each feature point $Y'''_t$ detected from the special light image is calculated on the basis of the feature value $y'''_t$ and the feature value $y'''_{t-1}$, which is a feature value of a corresponding feature point $Y'''_{t-1}$ of the frame one frame before, as indicated by being connected to each other using the horizontal lines.

Figure 14:
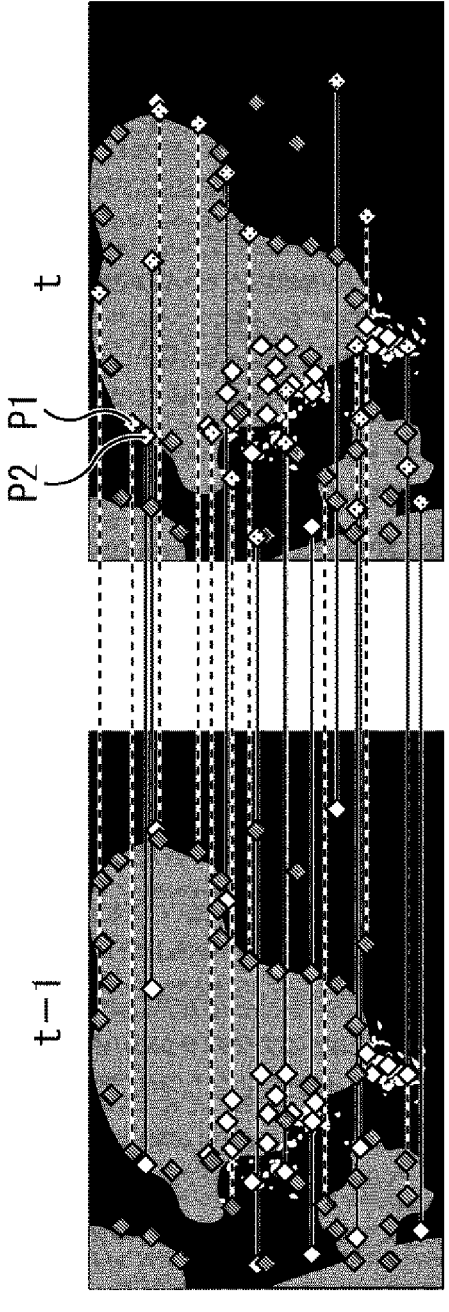
FIG. 14 is a diagram showing the feature points superimposed on the special light image.

FIG. 14 is a diagram showing the feature points superimposed on the special light image.

When the feature point $X''_{t-1}$ and the feature point $Y'''_{t-1}$ are superimposed on the special light image of the (t–1)-th frame, the image is as shown on the left of FIG. 14.

Meanwhile, when the feature point $X''_t$ and the feature point $Y'''_t$ are superimposed on the special light image of the t-th frame, the image is as shown on the right of FIG. 14. On the special light image of the t-th frame shown on the right of FIG. 14, not only the feature point $X''_t$ and the feature point $Y'''_t$ but also the feature point with high reliability among the feature point $X''_{t-1}$ and the feature point $Y'''_{t-1}$ are shown.

For example, the feature point at a position P1 is the feature point $Y'''_{t-1}$ with high reliability, and the feature point at a position P2 is the feature point $X''_{t-1}$ with high reliability. On the basis of the feature points shown on the special light image on the right of FIG. 14, a three-dimensional map at the time t is generated.

The three-dimensional map generation/position and posture estimation processing performed in Step S56 of FIG. 11 will be described with reference to the flowchart of FIG. 15.

As shown in FIG. 15, the processing from Steps S101 to S104 for the visible light image and the processing from Steps S105 to S108 for the special light image are performed in parallel, for example.

In Step S101, the three-dimensional map generation unit 83 of FIG. 10 acquires the visible light image supplied from the visible light development processing unit 91.

In Step S102, the three-dimensional map generation unit 83 extracts N feature points in each of the images of the t-th frame and the (t–1)-th frame and obtains feature value sets $\{x^1_t, \ldots, x^N_t\}$, $\{x^1_{t-1}, \ldots, x^N_{t-1}\}$ of the respective images.

In Step S103, the three-dimensional map generation unit 83 compares distances between the feature value $x''_t$ of the feature point $X''_t$ of the t-th frame and the extracted feature value set $\{x^1_{t-1}, \ldots, x^N_{t-1}\}$ of the (t–1)-th frame and searches for a corresponding feature point, which is a feature point with a smallest distance. The feature value of the corresponding feature point is $x''_{t-1}$.

For the distances $dx''_t$ $(x''_t, x''_{t-1})$, $dy'''_t$ $(y'''_t, y'''_{t-1})$, the Euclidean distance (L2 norm), the Hamming distance, and the like can be used. The distance $dx''_t$ $(x''_t, x''_{t-1})$ is a distance between the feature value $x''_t$ and the feature value $x''_{t-1}$. Further, the distance $dy'''_t$ $(y'''_t, y'''_{t-1})$ is a distance between the feature value $y'''_t$ and the feature value $y'''_{t-1}$.

In Step S104, the three-dimensional map generation unit 83 sets the reliability of the feature point $X''_t$ according to the smallness of the distance $dx''_t$ $(x''_t, x''_{t-1})$ between the feature value $x''_t$ of the feature point $X''_t$ of the t-th frame and the feature value $x''_{t-1}$ of a corresponding feature point of the (t–1)-th frame.

For the reliability, the value of the reciprocal of the distance may be used or a value obtained by combining the distance and a function such as a log may be used. Further, in order to adjust the degree of influence by the normal light and the special light, a predetermined coefficient may be set for the reliability of each light.

The processing described above is performed on each frame of the visible light image.

Meanwhile, in Step S105, the three-dimensional map generation unit 83 acquires the special light image obtained after the alignment, which is supplied from the alignment processing unit 92.

In Step S106, the three-dimensional map generation unit 83 extracts M feature points in each of the images of the t-th frame and the (t−1)-th frame and obtains feature value sets $\{y^1_t, \ldots, y^M_t\}$, $\{y^1_{t-1}, \ldots, y^M_{t-1}\}$ of the respective images.

In Step S107, the three-dimensional map generation unit 83 compares distances between the feature value $y^m_t$ of the feature point $Y^m_t$ of the t-th frame and the extracted feature value set $\{y^1_{t-1}, \ldots, y^M_{t-1}\}$ of the (t−1)-th frame and searches for a corresponding feature point, which is a feature point with a smallest distance. The feature value of the corresponding feature point is $y^m_{t-1}$.

In Step S108, the three-dimensional map generation unit 83 sets the reliability of the feature point $Y^m_t$ according to the smallness of the distance $dy^m_t$ ($y^m_t$, $y^m_{t-1}$) between the feature value $y^m_t$ of the feature point $Y^m_t$ of the t-th frame and the feature value $y^m_{t-1}$ of a corresponding feature point of the (t−1)-th frame.

The processing described above is performed on each frame of the special light image.

In Step S109, the three-dimensional map generation unit 83 arranges the feature point $X^n_t$ in the visible light image and the feature point $Y^m_t$ in the special light image respectively on the same planes of the t-th frame and the (t−1)-th frame.

In Step S110, the three-dimensional map generation unit 83 extracts the feature point set $\{Z^1_t, \ldots, Z^P_t\}$, which is the set of the top P feature points with higher reliability, among all the feature points $\{X^1_t, \ldots, X^N_t, Y^1_t, \ldots, Y^M_t\}$.

In Step S111, the three-dimensional map generation unit 83 estimates the positions of the endoscope 11 when the t-th frame and the (t−1)-th frame are imaged, and the three-dimensional positions of the feature point set $\{Z^1_t, \ldots, Z^P_t\}$, on the basis of the positions of the corresponding feature points in the t-th frame and the (t−1)-th frame, which are included in the feature point set $\{Z^1_t, \ldots, Z^P_t\}$ and the feature points constituting the three-dimensional map. The estimation of the position of the endoscope 11 and the three-dimensional positions of $\{Z^1_t, \ldots, Z^P_t\}$ proceeds while performing bundle adjustment.

In this case, the value seen as an outlier is removed from the feature point set $\{Z^1_t, \ldots, Z^P_t\}$ by using, for example, a method of random sample consensus (RANSAC). The feature point set from which the outlier is removed, becomes the feature point set $\{Z^1_t, \ldots, Z^{P'}_t\}$.

In Step S112, the three-dimensional map generation unit 83 adds the feature point set $\{Z^1_t, \ldots, Z^{P'}_t\}$ to the three-dimensional map in a case where a predetermined condition is satisfied. For example, the feature point set is added on the basis of a condition, e.g., the feature point set $\{Z^1_t, \ldots, Z^{P'}_t\}$ has sufficient reliability as compared with the past feature point.

The processing described above is repeated, thus performing the three-dimensional map generation/position and posture estimation processing.

Other three-dimensional map generation/position and posture estimation processing will be described with reference to the flowchart of FIG. 16.

The processing shown in FIG. 16 is different from the processing described with reference to FIG. 15 in the method of extracting the feature point set $\{Z^1_t, \ldots, Z^P_t\}$. In other words, the processing from Steps S121 to S129 and from Steps S131 to S132 is processing similar to the processing from Steps S101 to S109 and from Steps S111 to S112 of FIG. 15.

In Step S130, the three-dimensional map generation unit 83 selects the top Q feature points with higher reliability, among all the feature points $\{X^1_t, \ldots, X^N_t, Y^1_t, \ldots, Y^M_t\}$. Further, the three-dimensional map generation unit 83 counts the number of feature points of the visible light image and the number of feature points of the special light image, which are included in the Q feature points, and selects the feature point set $\{X^1_t, \ldots, X^N_t\}$ or $\{Y^1_t, \ldots, Y^M_t\}$, which includes a larger number of feature points. The three-dimensional map generation unit 83 extracts the top P feature points with higher reliability from the selected feature point set $\{X^1_t, \ldots, X^N_t\}$ or $\{Y^1_t, \ldots, Y^M_t\}$ and sets them as the feature point set $\{Z^1_t, \ldots, Z^P_t\}$.

As described above, the feature points can be selected by various methods and used as feature points constituting the three-dimensional map at the time t.

As described above, the combination SLAM using the visible light SLAM and the special light SLAM in combination performs the generation of a three-dimensional map and the estimation of a position and a posture, which allows an improvement in robustness. Using the results of the SLAM by a plurality of light sources allows an improvement in accuracy as compared with the case of using the results of the SLAM by a single light source.

It may be possible to switch between the feature points obtained as a result of the visible light SLAM and the feature points obtained as a result of the special light SLAM in accordance with the situation and to use the feature points as a result of the combination SLAM.

The three-dimensional map obtained by the visible light SLAM and the three-dimensional map obtained by the special light SLAM may be aligned on the basis of the estimation results of the position and the posture of the endoscope 11 by the combination SLAM such that one three-dimensional map is generated. It should be noted that the alignment of the three-dimensional maps obtained by the visible light SLAM and the special light SLAM may be performed using machine learning. For example, a feature value of the visible light SLAM and a feature value of the special light SLAM to be paired with the feature value of the visible light SLAM are input, as learning data labeled in advance, to the machine learning model of a multi-layer neural network, to generate parameters. Subsequently, the feature value obtained by the visible light SLAM and the feature value obtained by the special light SLAM may be input to an algorithm for alignment, which is set on the basis of the machine learning model and the parameters, thus performing the alignment.

The series of processing described above makes it possible to, in the special light SLAM using the edge of a blood vessel structure at a deep part or the like as a feature point, generate a three-dimensional map with few changes in a situation where treatment is performed during a surgery, and to constantly obtain SLAM results with high reliability.

In the special light SLAM using special light with high transmissivity, SLAM results using the latest information can be constantly obtained even if information of visible light is difficult to obtain due to mist, haze, or the like.

In the special light SLAM using the polarized light, the feature point in the specular reflection region can be detected from the special light image, and SLAM results can be obtained.

Modified Example

The combination SLAM may be performed using the visible light and a plurality of types of special light. In this case, the plurality of types of special light of different wavelength bands is used and imaging is performed during the irradiation with each of the types of special light, to generate various types of special light images. The combination SLAM is performed on the basis of the feature point detected from the visible light image and the feature point detected from each special light image.

As described above, the number of special light to be used in the combination SLAM can be set to be more than one.

Application Example

<System Configuration>

Next, with reference to FIG. 17, description will be given on an example of a case where a video microscope apparatus for surgery including an arm is used as an application example of a surgery support system according to an embodiment of the present technology.

Figure 17:
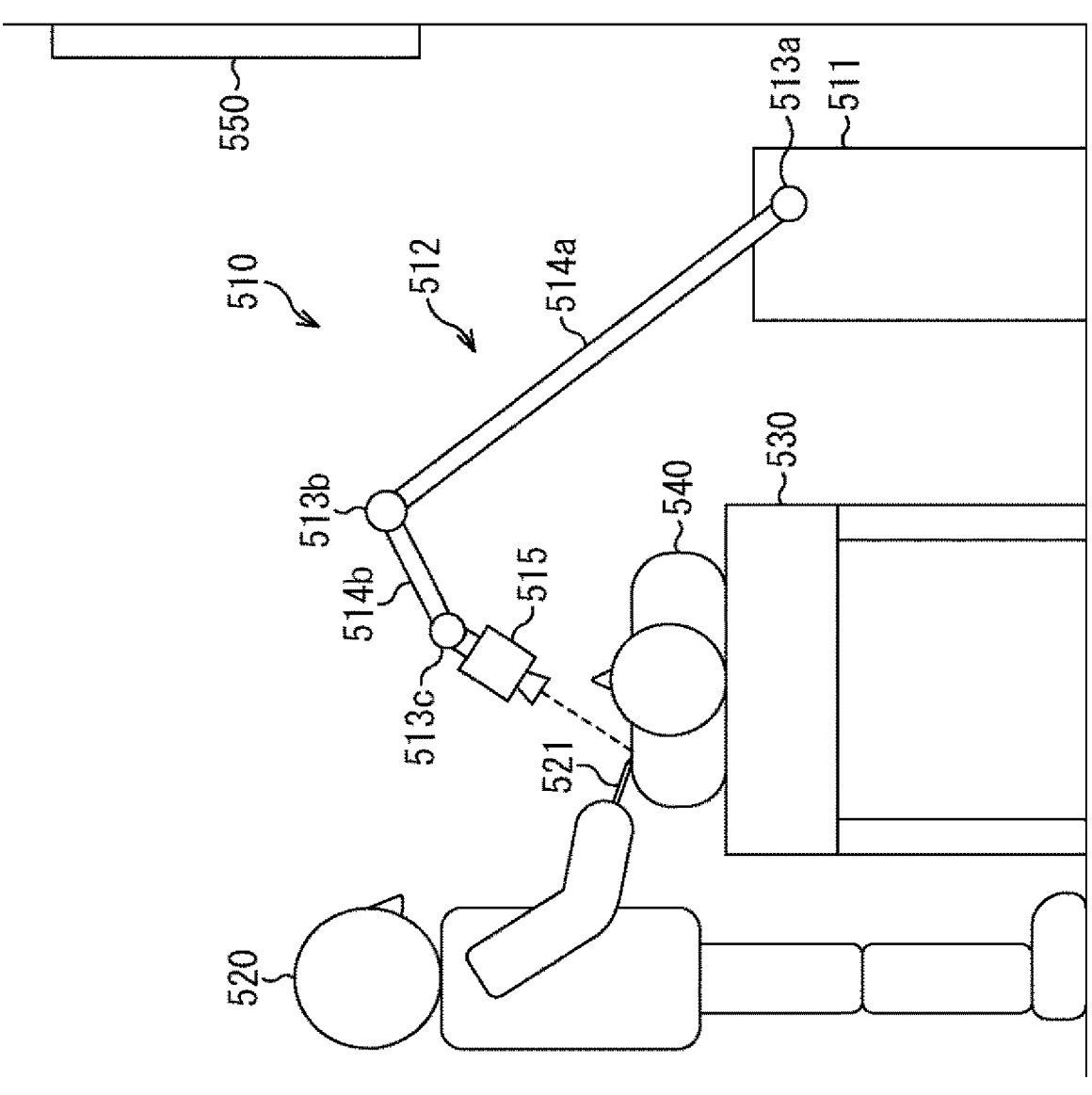
FIG. 17 is a diagram showing another configuration example of a surgery support system according to the embodiment of the present technology.

FIG. 17 shows an example of a microscope surgery system using a video microscope apparatus for surgery as an observation medical apparatus for observing the inside of the body of a patient.

FIG. 17 shows a state where a doctor as an operator (user) 520 is performing a surgery on a subject to be operated (patient) 540 lying on an operating table 530 by using, for example, surgical tools 521 such as a scalpel, tweezers, and forceps.

It should be noted that, in the following description, the operation is a generic term for various types of medical treatment such as a surgery and inspections, which are performed on a patient as the subject to be operated 540 by the doctor as the user 520. Further, while the example of FIG. 17 shows a situation of a surgery as an example of the operation, the operation using a video microscope apparatus for surgery 510 is not limited to a surgery and may be any other operations.

The video microscope apparatus for surgery 510 according to the embodiment of the present technology is provided beside the operating table 530.

The video microscope apparatus for surgery 510 includes a base portion 511 as a base, an arm portion 512 that extends from the base portion 511, and an imaging unit 515 connected, as a tip unit, to the tip of the arm portion 512.

The arm portion 512 includes a plurality of joints 513a, 513b, and 513c, a plurality of links 514a and 514b coupled to each other by the joints 513a and 513b, and the imaging unit 515 provided to the tip of the arm portion 512.

For simple description, the arm portion 512 includes the three joints 513a to 513c and the two links 514a and 514b in the example of FIG. 17. Actually, while considering the degree of freedom for the positions and postures of the arm portion 512 and the imaging unit 515, the number and the shape of the joints 513a to 513c and the links 514a and 514b, the direction of the drive shaft of the joints 513a to 513c, or the like may be appropriately set to achieve a desired degree of freedom.

The joints 513a to 513c have the function of rotatably coupling the links 514a and 514b to each other. When the joints 513a to 513c are rotationally driven, the drive of the arm portion 512 is controlled.

The imaging unit 515 is connected, as a tip unit, to the tip of the arm portion 512.

The imaging unit 515 is a unit that includes an optical system, which acquires an optical image of an object, and thus acquires an image of an object to be imaged, and is, for example, configured to be a camera capable of capturing moving images and still images. As shown in FIG. 17, the video microscope apparatus for surgery 510 controls the positions and the postures of the arm portion 512 and the imaging unit 515 such that the imaging unit 515 provided to the tip of the arm portion 512 images a state of an operation site of the subject to be operated 540.

It should be noted that the configuration of the imaging unit 515 connected, as a tip unit, to the tip of the arm portion 512 is not particularly limited. For example, the imaging unit 515 may be configured as an endoscope or a microscope. Further, the imaging unit 515 may be configured to be detachable from the arm portion 512.

For example, such a configuration may allow the imaging unit 515 corresponding to a use application to be appropriately connected, as a tip unit, to the tip of the arm portion 512. It should be noted that the case where the imaging unit 515 is applied as a tip unit is mainly described here, but it goes without saying that the tip unit to be connected to the tip of the arm portion 512 is not necessarily limited to the imaging unit 515.

Further, a display apparatus 550 such as a monitor or a display is installed at a position facing the user 520. An image of the operation site, which is acquired by the imaging unit 515, is displayed as an electrical image on a display screen of the display apparatus 550, for example, after an image processing apparatus built in or externally provided to the video microscope apparatus for surgery 510 performs various types of image processing on the image.

Such a configuration allows the user 520 to perform various types of treatment (for example, surgery) while viewing the electrical image of the operation site, which is displayed on the display screen of the display apparatus 550.

Here, in the example of FIG. 17, the imaging unit 515 includes, for example, the imaging unit 51 described with reference to FIG. 3 and the like. Further, the image processing apparatus that performs various types of image processing on the image of the operation site acquired by the imaging unit 515 corresponds to an example of the information processing unit 71 described with reference to FIG. 3 and the like.

<Hardware Configuration>

Next, an example of a hardware configuration of an information processing apparatus constituting the surgery support system according to the embodiment of the present technology will be described in details with reference to FIG. 18.

Figure 18:
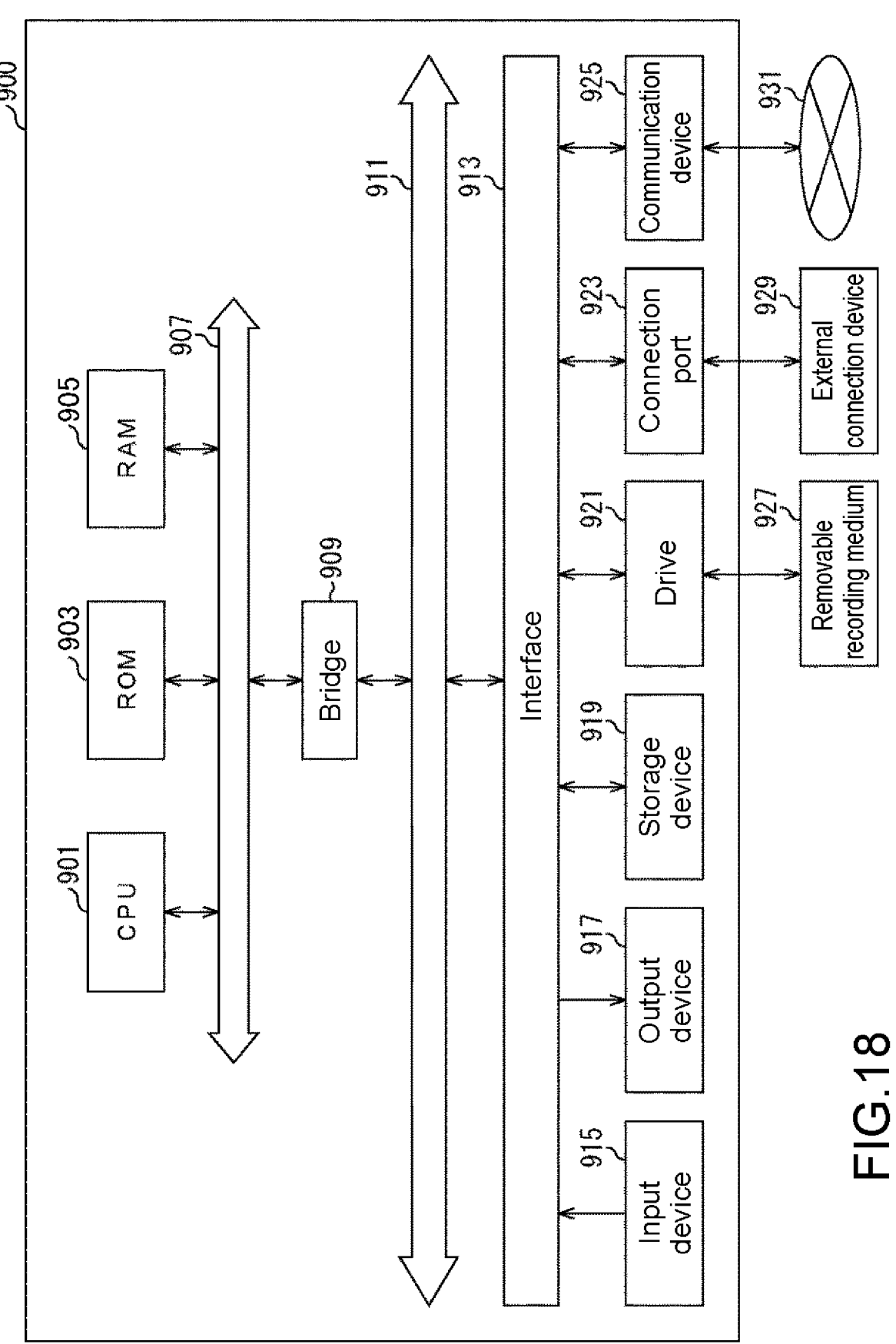
FIG. 18 is a block diagram showing a hardware configuration example of an information processing apparatus.

FIG. 18 is a block diagram showing an example of a hardware configuration of an information processing apparatus 900 constituting the surgery support system according to the embodiment of the present technology.

As shown in FIG. 18, the information processing apparatus 900 includes a CPU 901, a ROM 903, and a RAM 905. Additionally, the information processing apparatus 900 includes a host bus 907, a bridge 909, an external bus 911, an interface 913, an input device 915, an output device 917, and a storage device 919. It should be noted that the information processing apparatus 900 may include a drive 921, a connection port 923, and a communication device 925.

The CPU 901 functions as an arithmetic processing device and a control device and controls all or part of the operation in the information processing apparatus 900 according to various programs recorded in the ROM 903, the RAM 905, or the storage device 919 or on a removable recording medium 927.

The ROM 903 stores programs to be used by the CPU 901, arithmetic parameters, and the like. The RAM 905 temporarily stores programs to be used by the CPU 901, parameters that appropriately change during execution of a program, and the like. Those components are connected to one another by the host bus 907 configured by an internal bus such as a CPU bus. It should be noted that the configurations in the information processing unit 71 described with reference to FIG. 3 and the like are achieved by, for example, the CPU 901.

The host bus 907 is connected to the external bus 911, such as a peripheral component interconnect/interface (PCI) bus, via the bridge 909. The input device 915, the output device 917, the storage device 919, the drive 921, the connection port 923, and the communication device 925 are connected to the external bus 911 via the interface 913.

The input device 915 is operation means for the user to operate, such as a mouse, a keyboard, a touch panel, a button, a switch, a lever, and a pedal. Further, the input device 915 may be, for example, remote control means (so-called remote controller) using infrared rays or other electrical waves. The input device 915 may be, for example, an external connection device 929 such as a mobile phone, a smartphone, or a tablet terminal, which corresponds to the operation of the information processing apparatus 900.

The input device 915 includes, for example, an input control circuit that generates an input signal on the basis of the information input by the user with the above-mentioned operation means and outputs the input signal to the CPU 901.

By operating the input device 915, the user can input various types of data and give instructions for operations to be processed, with respect to the information processing apparatus 900.

The output device 917 includes a device capable of visually or aurally notifying the user of acquired information. Specifically, the output device 917 is configured as a display device such as a cathode-ray tube (CRT) display device, a liquid crystal display device, a plasma display device, an electroluminescence (EL) display device, or a lamp, a sound output device such as a speaker and headphones, a printer device, and the like.

The output device 917 outputs, for example, results obtained from various types of processing performed by the information processing apparatus 900. Specifically, the display device displays the results obtained from various types of processing performed by the information processing apparatus 900 in texts or images. Meanwhile, the sound output device converts audio signals, which include reproduced sound data or acoustic data, into analog signals for output.

The storage device 919 is a device for storing data and is configured as an example of a storage unit of the information processing apparatus 900. The storage device 919 includes, for example, a magnetic storage device such as a hard disk drive (HDD), a semiconductor storage device, an optical storage device, or a magneto-optical storage device. The storage device 919 stores programs to be executed by the CPU 901, various types of data, and the like.

The drive 921 is a reader/writer for a recording medium and is built in or externally provided to the information processing apparatus 900. The drive 921 reads information recorded on the removable recording medium 927 such as a mounted magnetic disk, optical disc, magneto-optical disk, or semiconductor memory, and outputs the information to the RAM 905. Further, the drive 921 is also capable of writing a record on the removable recording medium 927 such as a mounted magnetic disk, optical disc, magneto-optical disk, or semiconductor memory.

The removable recording medium 927 is, for example, a DVD™ medium, an HD-DVD™ medium, or a Blu-ray™ medium. Further, the removable recording medium 927 may be a compact flash (CF)™, a flash memory, a secure digital (SD) memory card, or the like. Additionally, the removable recording medium 927 may be, for example, an integrated circuit (IC) card including a contactless IC chip, or an electronic apparatus.

The connection port 923 is a port for directly connecting the external connection device 929 to the information processing apparatus 900. Examples of the connection port 923 include a universal serial bus (USB) port, an IEEE1394 port, and a small computer system interface (SCSI) port. Other examples of the connection port 923 include an RS-232C port, an optical audio terminal, a high-definition multimedia interface (registered trademark) (HDMI) port. When the external connection device 929 is connected to the connection port 923, the information processing apparatus 900 directly acquires various types of data from the external connection device 929 or provides various types of data to the external connection device 929.

The communication device 925 is, for example, a communication interface including a communication device for connecting to a communication network 931. The communication device 925 is, for example, a communication card for a wired or wireless local area network (LAN), Bluetooth (registered trademark), or wireless USB (WUSB). Further, the communication device 925 may be a router for optical communication, a router for asymmetric digital subscriber line (ADSL), or a modem for various communications.

The communication device 925 is capable of transmitting and receiving signals to and from the Internet or other communication devices according to a predetermined protocol such as TCP/IP, for example. Further, the communication network 931 connected to the communication device 925 may be configured by the network connected in a wired or wireless manner. The communication network 931 may be, for example, the Internet or a home LAN or may be a communication network for infrared communication, radio communication, or satellite communication.

The constituent elements of the information processing apparatus 900 of FIG. 18 may be constituted using general-purpose members or may be constituted by hardware dedicated to the functions of the constituent elements. Thus, a hardware configuration to be used can be appropriately changed according to a technical level when the embodiment of the present technology is performed.

Additionally, it may be possible to produce computer programs for achieving the functions of the information processing apparatus 900 constituting the surgery support system according to the embodiment of the present technology and to implement the computer programs in a personal computer or the like. Further, it may also be possible to provide a computer-readable recording medium in which such computer programs are stored. The recording medium is, for example, a magnetic disk, an optical disc, a magneto-optical disk, or a flash memory. Further, the computer programs may be distributed, for example, via a network without using the recording medium.

It should be noted that the program to be executed by the computer may be a program that is processed chronologically along the described order in this specification or may be a program that is processed in parallel or at a necessary timing such as when an invocation is performed.

<Others>

In this specification, a system means an aggregation of a plurality of constituent elements (apparatuses, devices, modules (parts), and the like), regardless of whether all constituent elements are included in the same casing or not. Therefore, a plurality of apparatuses accommodated in separate casings and connected to one another via a network is a system, and one apparatus including a plurality of modules in one casing is also a system.

It should be noted that the effects disclosed in this specification are merely exemplary ones and are not restrictive ones, and any other effects may be produced.

The embodiment of the present technology is not limited to the embodiment described above and can be variously modified without departing from the gist of the present technology.

For example, the present technology can have a configuration of cloud computing in which a plurality of apparatuses share one function and cooperate to perform processing via a network. Also, the present technology can have a configuration of server computing coupled to the medical imaging device via a network. Also, the present technology can have a configuration of a converter that converts signals output from the medical imaging device into IP (Internet protocol) signals. In other words, some or all of the functions of the CCU can be put on the server or the converter.

Further, each step described in the flowcharts described above can be executed by one apparatus or shared and executed by a plurality of apparatuses.

Additionally, in the case where one step includes a plurality of processing steps, the plurality of processing steps in one step can be executed by one apparatus or shared and executed by a plurality of apparatuses.

Combination Examples of Configurations

The present technology can have the following configurations.

(1)
A medical observation system, including:
an imaging unit that captures an image of a surgical field;
a light source unit that irradiates the surgical field with observation light of a predetermined wavelength band or special light of a wavelength band different from the predetermined wavelength band; and
a controller that generates three-dimensional information on the basis of a special light image captured by the imaging unit during irradiation with the special light.

(2)
The medical observation system according to (1), in which
the controller
generates the three-dimensional information, the three-dimensional information indicating a shape of a space including the surgical field, and
estimates, on the basis of the generated three-dimensional information, a position and a posture of the imaging unit when the special light image is captured.

(3)
The medical observation system according to (1) or (2), further including:
a development processing unit that generates an observation image on the basis of a signal supplied from the imaging unit after the imaging unit captures the image of the surgical field during irradiation with the special light; and
a display controller that causes the observation image to be displayed, the observation image corresponding to estimation results of a position and a posture of the imaging unit.

(4)
The medical observation system according to (1) or (2), in which
the imaging unit includes
an observation-light imaging device that is an imaging device for the observation light, and
a special-light imaging device that is an imaging device for the special light.

(5)
The medical observation system according to (4), further including:
a development processing unit that generates an observation image on the basis of a signal supplied from the imaging unit after the observation-light imaging device captures an image of the surgical field during irradiation with the observation light; and
a display controller that causes the observation image to be displayed, the observation image corresponding to estimation results of the position and the posture of the imaging unit.

(6)
The medical observation system according to (5), in which
the controller generates the three-dimensional information on the basis of the special light image captured by the special-light imaging device during irradiation with the special light and an observation light image captured by the observation-light imaging device during irradiation with the observation light.

(7)
The medical observation system according to (6), in which
the controller generates the three-dimensional information including a feature point in the special light image and a feature point in the observation light image.

(8)
The medical observation system according to (7), in which
the controller
calculates reliability of the feature point in the special light image and reliability of the feature point in the observation light image on the basis of feature values of the respective feature points, and
generates the three-dimensional information by using a predetermined number of feature points with high reliability as feature points of the three-dimensional information.

(9)
The medical observation system according to any one of (1) to (8), in which
the wavelength band of the special light is longer than the predetermined wavelength band of the observation light.

(10)
The medical observation system according to any one of (1) to (8), in which
the observation light includes light to be reflected on a surface of the surgical field, and the special light includes light to be reflected on a structure at a deep part of the surgical field.

(11)
The medical observation system according to any one of (1) to (8), in which
the observation light includes light to be reflected on a surface of the surgical field, and the special light includes light to be reflected on a blood vessel of the surface of the surgical field.

(12)

The medical observation system according to any one of (1) to (8), in which the special light includes light obtained through a polarization filter.

(13)

The medical observation system according to any one of (1) to (8), in which the special light includes light having a predetermined pattern, with which the surgical field is to be irradiated.

(14)

The medical observation system according to any one of (1) to (8), in which the special light includes light obtained by pulse-modulating light of a predetermined wavelength.

(15)

A medical observation method for a medical observation system, the method including:

capturing, by an imaging unit, an image of a surgical field;

irradiating, by a light source unit, the surgical field with observation light of a predetermined wavelength band or special light of a wavelength band different from the predetermined wavelength band; and generating, by a controller, three-dimensional information on the basis of a special light image captured by the imaging unit during irradiation with the special light.

(16)

An information processing apparatus, including a controller that generates three-dimensional information on the basis of a special light image, the special light image being obtained by capturing an image of a surgical field during irradiation with special light from a light source unit that irradiates the surgical field with observation light of a predetermined wavelength band or the special light of a wavelength band different from the predetermined wavelength band.

The present technology can also have the following configurations.

(1)

A medical imaging system including:

a light source configured to irradiate a surgical field with observation light of a first wavelength band or special light of a second wavelength band different from the first wavelength band;

an image capture device configured to generate a special light image based on reflected special light that is the special light reflected from at least a portion of the surgical field and received by the image capture device; and a control processing circuit configured to generate three-dimensional information including three-dimensional coordinate information about the surgical field based on the special light image.

(2)

The medical imaging system according to (1), wherein:

the reflected special light includes the special light that is reflected from a portion of the surgical field that is below an outer surface of the surgical field;

the image capture device is configured to generate the special light image based on the reflected special light that is the special light reflected from the portion of the surgical field that is below an outer surface of the surgical field, the special light image including information regarding the portion of the surgical field that is below the outer surface of the surgical field; and the control processing circuit is further configured to generate the three-dimensional information based on the information regarding the portion of the surgical field that is below the outer surface of the surgical field.

(3)

The medical imaging system according to (1), wherein:

the outer surface of the surgical field is arranged between the special light image capture device and the portion of the surgical field that is below the outer surface of the surgical field along an optical axis of the reflected special light received by the image capture device.

(4)

The medical imaging system according to (1), wherein:

the image capture device is included within an endoscope; and the control processing circuit is further configured to estimate a position and posture of a portion of the endoscope with respect to the surgical field based on the generated three-dimensional information.

(5)

The medical imaging system according to (4), further comprising:

a stored image memory configured to store a first three-dimensional image of a portion of the surgical field obtained before a start of a surgical procedure; and a display controlling circuit, wherein the control processing circuit is further configured to generate a second three-dimensional image of the portion of the surgical field based on the first three-dimensional image and the estimated position and posture of the portion of the endoscope, and the display controlling circuit is configured to control a display of a two-dimensional image based on the second three-dimensional image.

(6)

The medical imaging system according to (1), wherein:

the light of the first wavelength band is visible light; and the light of the second wavelength band is IR light.

(7)

The medical imaging system according to (1), wherein:

the three-dimensional information about the surgical field includes information about a three-dimensional shape of a space including the surgical field inside a body of a patient.

(8)

The medical imaging system according to (6), further comprising:

the image capture device generates a visible light image based on reflected visible light that is the visible light reflected from at least the portion of the surgical field and received by the visible image capture device; and the control processing circuit is further configured to perform an alignment processing to adjust the special light image so that the adjusted special light image is aligned with the visible light image.

(9)

The medical imaging system according to (8), wherein:

the control processing circuit is further configured to determine a reliability of feature points in each of the special light image and the visible light image; and the control processing circuit is further configured to generate the three-dimensional information based on the determined reliability of the feature points in each of the special light image and the visible light image.

(10)

The medical imaging system according to (9), wherein:

the control processing circuit is further configured to generate the three-dimensional information by retaining only feature points having a relatively high reliability.

(11)

The medical imaging system according to (10), wherein:

the control processing circuit is further configured to generate a three-dimensional map based on the three-dimensional information.

(12)

The medical imaging system according to (1), wherein the control processing circuit is configured to:

generates the three-dimensional information, the three-dimensional information indicating a shape of a space including the surgical field, and estimates, on a basis of the generated three-dimensional information, a position and a posture of the imaging capture device when the special light image is captured.

(13)

The medical imaging system according to (1), wherein the control processing circuit is further configured to:

generate an observation image on a basis of a signal supplied from the image capture device after the image capture device captures the special light image of the surgical field during irradiation with the special light; and cause the observation image to be displayed, the observation image corresponding to estimation results of a position and a posture of the image capture device.

(14)

The medical imaging system according to (1), wherein the control processing circuit is further configured to:

generate an observation image on a basis of a signal supplied from the image capture device after the image capture device captures an image of the surgical field during irradiation with the observation light; and cause the observation image to be displayed, the observation image corresponding to estimation results of the position and the posture of the image capture device.

(15)

The medical imaging system according to (14), wherein the control processing circuit is further configured to:

generate the three-dimensional information on a basis of the special light image captured by the special-light imaging device during irradiation with the special light and an observation light image captured by the observation-light imaging device during irradiation with the observation light.

(16)

The medical imaging system according to (15), wherein the control processing circuit is further configured to:

generate the three-dimensional information including a feature point in the special light image and a feature point in the observation light image.

(17)

The medical imaging system according to (16), wherein the control processing circuit is further configured to:

calculate reliability of the feature point in the special light image and reliability of the feature point in the observation light image on a basis of feature values of the respective feature points, and generate the three-dimensional information by using a predetermined number of feature points with high reliability as feature points of the three-dimensional information.

(18)

The medical imaging system according to (1), wherein the control processing circuit is included a IP converter coupled to the image capture device.

(19)

A medical imaging processing method including:

obtaining a first image data captured when a first wavelength band of light is irradiated and a second image data captured when a second wavelength band of light is irradiated, wherein the first wavelength band is different from the second wavelength band, and generating three-dimensional information including three-dimensional coordinate information about a surgical field based on the second image data.

(20)

A medical information processing apparatus including:

control processing circuitry configured to:

obtain a first image data captured when a first wavelength band of light is irradiated and a second image data captured when a second wavelength band of light is irradiated, wherein the first wavelength band is different from the second wavelength band, and generate three-dimensional information including three-dimensional coordinate information about a surgical field based on the second image data.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 1 medical observation system (medical imaging system)
11 endoscope (medical imaging device)
13 CCU (medical processing apparatus)
15 display apparatus
17 light source apparatus
51 imaging unit
61 special light irradiation unit
62 image sensor for special light
63 visible light irradiation unit
64 image sensor for visible light
71 information processing unit
81 special light development processing unit
82 development processing unit for special light observation
83 three-dimensional map generation unit
84 three-dimensional map storage unit
85 on-screen position calculation unit
86 three-dimensional information storage unit
87 display controller
91 visible light development processing unit
92 alignment processing unit

The invention claimed is:

1. A medical imaging system comprising:

a light source configured to irradiate a medical observation field with observation light of a first wavelength band and to irradiate the medical observation field with special light of a second wavelength band different from the first wavelength band;

an image sensor configured to generate a special light image based on reflected special light that is the special light reflected from at least a portion of the medical observation field and received by the image sensor, wherein the reflected special light includes special light reflected from the portion of the medical observation field that is below a surface of the medical observation field from which the observation light is reflected; and a control processing circuit configured to generate, by performing Simultaneous Localization and Mapping (SLAM) based on feature points of sub-surface structures appearing in the special light image, three-dimensional information including three-dimensional coordinate information about the medical observation field based on the special light image including information regarding the portion of the surgical field that is below the surface of the medical observation field from which the observation light is reflected.

2. The medical imaging system according to claim 1, wherein:

the observation light is reflected from an outer surface of the medical observation field.

3. The medical imaging system according to claim 1, wherein:

the image sensor is included within an endoscope; and the control processing circuit is further configured to estimate a position and posture of a portion of the endoscope with respect to the medical observation field based on the generated three-dimensional information.

4. The medical imaging system according to claim 3, further comprising:

a stored image memory configured to store a first three-dimensional image of a portion of the medical observation field obtained before a start of a medical observation procedure; and a display controlling circuit, wherein the control processing circuit is further configured to generate a second three-dimensional image of the portion of the medical observation field based on the first three-dimensional image and the estimated position and posture of the portion of the endoscope, and the display controlling circuit is configured to control a display of a two-dimensional image based on the second three-dimensional image.

5. The medical imaging system according to claim 1, wherein:

the light of the first wavelength band is visible light; and the light of the second wavelength band is infrared light.

6. The medical imaging system according to claim 5, further comprising:

the image sensor is configured to generate a visible light image based on reflected visible light that is the visible light reflected from at least the portion of the medical observation field and received by the image sensor; and the control processing circuit is further configured to perform an alignment processing to adjust the special light image so that the adjusted special light image is aligned with the visible light image.

7. The medical imaging system according to claim 6, wherein:

the control processing circuit is further configured to determine a plurality of feature points in each of the special light image and the visible light image; and the control processing circuit is further configured to generate the three-dimensional information based on the determined reliability of the feature points in each of the special light image and the visible light image.

8. The medical imaging system according to claim 7, wherein:

the control processing circuit is further configured to generate the three-dimensional information by retaining only feature points having a relatively high reliability.

9. The medical imaging system according to claim 8, wherein:

the control processing circuit is further configured to generate a three-dimensional map based on the three-dimensional information.

10. The medical imaging system according to claim 1, wherein:

the three-dimensional information about the medical observation field includes information about a three-dimensional shape of a space including the medical observation field inside a body of a patient.

11. The medical imaging system according to claim 1, wherein:

the three-dimensional information indicates a shape of a space including the medical observation field, and the control processing circuit is configured to estimate, on a basis of the generated three-dimensional information, a position and a posture of the image sensor when the special light image is captured.

12. The medical imaging system according to claim 1, wherein the control processing circuit is further configured to:

generate an observation image on a basis of a signal supplied from the image sensor after the image sensor captures the special light image of the medical observation field during irradiation with the special light; and cause the observation image to be displayed, the observation image corresponding to estimation results of a position and a posture of the image sensor.

13. The medical imaging system according to claim 1, wherein the control processing circuit is further configured to:

generate an observation image on a basis of a signal supplied from the image sensor after the image sensor captures an image of the medical observation field during irradiation with the observation light; and cause the observation image to be displayed, the observation image corresponding to estimation results of the position and the posture of the image sensor.

14. The medical imaging system according to claim 13, wherein the control processing circuit is further configured to:

generate the three-dimensional information on a basis of the special light image captured by the image sensor during irradiation with the special light and an observation light image captured by the image sensor during irradiation with the observation light.

15. The medical imaging system according to claim 14, wherein the control processing circuit is further configured to:

generate the three-dimensional information including a feature point in the special light image and a feature point in the observation light image.

16. The medical imaging system according to claim 15, wherein the control processing circuit is further configured to:

calculate reliability of the feature point in the special light image and reliability of the feature point in the observation light image on a basis of feature values of the respective feature points, and generate the three-dimensional information by using a predetermined number of feature points with high reliability as feature points of the three-dimensional information.

17. The medical imaging system according to claim 1, wherein the special light is polarized.

18. A medical imaging processing method comprising:

obtaining a first image data captured when a first wavelength band of light is irradiated onto a medical observation field and a second image data captured when a second wavelength band of light is irradiated onto the medical observation field, wherein the first wavelength band is different from the second wavelength band and the second wavelength band is reflected from a portion of the medical observation field below a surface of the medical observation field from which the first wavelength band is reflected, and generating, by performing Simultaneous Localization and Mapping (SLAM) based on feature points of subsurface structures appearing in the special light image, three-dimensional information including three-dimensional coordinate information about the medical observation field based on the second image data regarding the portion of the medical observation field that is below the surface of the medical observation field from which the first wavelength band is reflected.

19. The medical imaging method according to claim 18, wherein the second wavelength band of light is polarized.

20. A medical information processing apparatus comprising:

control processing circuitry configured to:

obtain a first image data captured when a first wavelength band of light is irradiated onto a medical observation field and a second image data captured when a second wavelength band of light is irradiated onto the medical observation field, wherein the first wavelength band is different from the second wavelength band and the second wavelength band is reflected from a portion of the medical observation field below a surface of the medical observation field from which the first wavelength band is reflected, and generate, by performing Simultaneous Localization and Mapping (SLAM) based on feature points of subsurface structures appearing in the special light image, three-dimensional information including three-dimensional coordinate information about the medical observation field based on the second image data regarding the portion of the medical observation field that is below the surface of the medical observation field from which the first wavelength band is reflected.

* * * * *